(12) United States Patent  
O'Sullivan et al.

(10) Patent No.: US 9,414,589 B2
(45) Date of Patent: Aug. 16, 2016

(54) N-CYCLYLAMIDES AS NEMATICIDES

(71) Applicant: SYNGENTA PARTICIPATIONS AG, Basel (CH)

(72) Inventors: Anthony Cornelis O'Sullivan, Stein (CH); Olivier Loiseleur, Stein (CH); Roman Staiger, Stein (CH); Torsten Luksch, Stein (CH); Thomas Pitterna, Stein (CH)

(73) Assignee: Syngenta Participations AG, Basel (CH)

( * ) Notice: Subject to any disclaimer, the term of this patent is extended or adjusted under 35 U.S.C. 154(b) by 16 days.

(21) Appl. No.: 14/382,555

(22) PCT Filed: Mar. 6, 2013

(86) PCT No.: PCT/EP2013/054461
§ 371 (c)(1),
(2) Date: Sep. 3, 2014

(87) PCT Pub. No.: WO2013/143811
PCT Pub. Date: Oct. 3, 2013

(65) Prior Publication Data
US 2015/0045213 A1 Feb. 12, 2015

(30) Foreign Application Priority Data
Mar. 26, 2012 (EP) .................... 12161190

(51) Int. Cl.
| A01N 37/18 | (2006.01) |
|---|---|
| C07D 405/14 | (2006.01) |
| C07C 211/37 | (2006.01) |
| A61K 31/166 | (2006.01) |
| A61K 31/337 | (2006.01) |
| A01N 43/20 | (2006.01) |
| A01N 43/40 | (2006.01) |
| A01N 43/50 | (2006.01) |
| A01N 43/54 | (2006.01) |
| C07D 213/81 | (2006.01) |
| C07D 305/08 | (2006.01) |
| C07D 407/12 | (2006.01) |
| C07C 255/58 | (2006.01) |
| C07D 213/82 | (2006.01) |
| C07D 239/28 | (2006.01) |
| C07D 405/10 | (2006.01) |
| C07D 239/30 | (2006.01) |
| C07D 405/12 | (2006.01) |
| C07D 241/24 | (2006.01) |
| C07C 233/66 | (2006.01) |
| C07C 233/67 | (2006.01) |
| C07D 307/68 | (2006.01) |
| C07C 251/48 | (2006.01) |
| C07C 231/10 | (2006.01) |
| C07C 251/44 | (2006.01) |

(52) U.S. Cl.
CPC ............... *A01N 37/18* (2013.01); *A01N 43/20* (2013.01); *A01N 43/40* (2013.01); *A01N 43/50* (2013.01); *A01N 43/54* (2013.01); *A61K 31/166* (2013.01); *A61K 31/337* (2013.01); *C07C 211/37* (2013.01); *C07C 231/10* (2013.01); *C07C 233/66* (2013.01); *C07C 233/67* (2013.01); *C07C 251/44* (2013.01); *C07C 251/48* (2013.01); *C07C 255/58* (2013.01); *C07D 213/81* (2013.01); *C07D 213/82* (2013.01); *C07D 239/28* (2013.01); *C07D 239/30* (2013.01); *C07D 241/24* (2013.01); *C07D 305/08* (2013.01); *C07D 307/68* (2013.01); *C07D 405/10* (2013.01); *C07D 405/12* (2013.01); *C07D 405/14* (2013.01); *C07D 407/12* (2013.01); *C07C 2101/04* (2013.01)

(58) Field of Classification Search
CPC .. C07C 211/37; C07C 231/10; C07C 233/66; C07C 233/67; C07C 251/44; C07C 251/48; C07C 255/58; C07C 2101/04; C07D 213/81; C07D 213/82; C07D 239/28; C07D 239/30; C07D 241/24; C07D 305/08; C07D 307/68; C07D 405/10; C07D 405/12; C07D 405/14; C07D 407/12; A01N 37/18; A01N 43/20; A01N 43/40; A01N 43/50; A01N 43/54; A61K 31/166; A61K 31/337
See application file for complete search history.

(56) References Cited

U.S. PATENT DOCUMENTS 7,674,474 B2 * 3/2010 Chou ................ A01N 43/36
424/405

FOREIGN PATENT DOCUMENTS

| WO | 2006122952 A1 | 11/2006 |
|---|---|---|
| WO | 2006122955 A1 | 11/2006 |

OTHER PUBLICATIONS

XP-002676719, Database CA, Chemical Abstracts Service, Columbus, Ohio; US, Burger, Alfred et al., "2-Arylcyclobutylamines and -amino acids", retrieved from STN Database accession No. 1967:443491.*

(Continued)

*Primary Examiner* — Jane C Oswecki
(74) *Attorney, Agent, or Firm* — Brian D. McAlhaney

(57) ABSTRACT

Compounds of the formula (I), in which the substituents are as defined in claim 1, are suitable for use as nematicides.

(I)

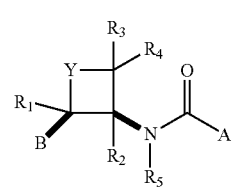

19 Claims, No Drawings

(56) References Cited

OTHER PUBLICATIONS

"Prevention", Merriam-Webster Online Dictionary [online], [retrieved Feb. 7, 2015] Retrieved from the Internet: <URL:http://www.merriam-webster.com/dictionary/prevention.*

XP-002676719, Database CA, Chemical Abstracts Service, Columbus, Ohio, US, Burger, Alfred et al., "2-Arylcyclobutylamines and -amino acids", retrieved from STN Database accession No. 1967:443491.

Nichols et al., J. Med. Chem., 1984, 27, 9, 1108-1111.

International Search Report for International Application No. PCT/EP2013/054461, May 17, 2013.

* cited by examiner

N-CYCLYLAMIDES AS NEMATICIDES

This application is a 371 filing of International Application No. PCT/EP2013/054461, filed Mar. 6, 2013, which claims priority benefit to European Patent No. 12161190.9 filed Mar. 26, 2012, the contents of all of which are incorporated herein by reference.

The present invention relates to novel cyclobutylcarboxamide compounds, a process for the preparation of these compounds and their use as nematicides.

Cyclalkylcarboxamides are described, for example, in WO 09/043,784, WO06/122952, WO06/122955, WO05/103006, WO05/103004 and WO04/014842.

Novel cyclobutylcarboxamides have now been found characterized by a cis substituted cyclobutyl ring, which show good nematicidal activity.

The present invention thus relates to compounds of the formula I

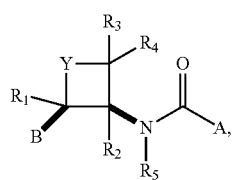

(I)

wherein
Y is O, C=O, or CR12R13;
A is a 5- or 6-membered heteroaromatic ring containing 1 to 3 heteroatoms, each independently selected from oxygen, nitrogen and sulphur, or a phenyl ring, the heteroaromatic ring or the phenyl being optionally substituted by one or more R6;
R6 is, independently of each other, halogen, cyano, C1-C4-alkyl, C1-C4-haloalkyl, C1-C4-alkoxy, C1-C4-haloalkoxy, C1-C4-haloalkylthio, C1-C4-alkoxy-C1-C4-alkyl or C1-C4-haloalkoxy-C1-C4-alkyl;
R1, R2, R3, R4, R12 and R13, independently of each other, are hydrogen, halogen, cyano, C1-C4-alkyl, C1-C4-alkoxy or C1-C4-haloalkyl;
R5 is hydrogen, methoxy or hydroxyl;
B is phenyl substituted by one or more R8;
R8 is, independently of each other, halogen, cyano or a group -L-R9, where each L is independently of each other a bond, —O—, —OC(O)—, —NR7-, —NR7CO—, —NR7S(O)n-, —S(O)n-, —S(O)nNR7-, —COO— or CONR7-;
n is 0, 1 or 2;
R7 is hydrogen, C1-C4-alkyl, C1-C4-haloalkyl, benzyl or phenyl, where benzyl and phenyl is unsubstituted or substituted with halogen, cyano, C1-C4-alkyl or C1-C4-haloalkyl;
R9 is, independently of each other, C1-C6-alkyl, which is unsubstituted or substituted by one or more R10, C3-C6-cycloalkyl, which is unsubstituted or substituted by one or more R10, C6-C14-bicycloalkyl, which is unsubstituted or substituted by one or more R10, C2-C6-alkenyl, which is unsubstituted or substituted by one or more R10, C2-C6-alkynyl, which is unsubstituted or substituted by one or more R10, phenyl, which is unsubstituted or substituted by R10, or heteroaryl, which is unsubstituted or substituted by one or more R10;
R10 is, independently of each other, halogen, cyano, C1-C4-alkyl, C1-C4-haloalkyl, C1-C4-alkoxy, C1-C4-haloalkoxy, C1-C4-alkylthio, C1-C4-haloalkylthio, C3-C6-alkenyloxy, or C3-C6-alkynyloxy;

wherein B and A-CO—NR5 are cis to each other on the four-membered ring,
and tautomers/isomers/enantiomers of these compounds.

The compounds of formula (I) and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case. This invention accordingly covers all such isomers and tautomers and mixtures thereof in all proportions as well as isotopic forms such as deuterated compounds. As an example, the compounds of the invention may contain one or more asymmetric carbon atoms, for example, at the —CR³R⁴— group or Y in —CR¹²CR¹³— or on its substituents, and the compounds of formula (I) may exist as enantiomers (or as pairs of diastereoisomers) or as mixtures of such.

The invention also covers salts and N-oxides of each compound for formula (I).

One skilled in the art also recognizes that because in the environment and under physiological conditions salts of chemical compounds are in equilibrium with their corresponding non salt forms, salts share the biological utility of the non salt forms.

Thus a wide variety of salts of compounds of the invention (and active ingredients used in combination with the active ingredients of the invention) may be useful for control of invertebrate pests and animal parasites. Salts amongst agriculturally and/or physiologically tolerable salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Suitable amongst agriculturally and/or physiologically tolerable salts can also be the salts of those cations which do not adversely affect the pesticidal and/or parasiticidal action of the compounds of formula (I). Thus, especially suitable cations are the ions of the alkali metals including sodium, potassium and lithium, of the alkaline earth metals including calcium and magnesium, and of the transition metals including manganese, copper, iron, zinc, cobalt, lead, silver, nickel, and also ammonium or organic ammonium including monoalkylammonium, dialkylammonium, trialkylammonium, tetraalkylammonium, monoalkenylammonium, dialkenylammonium, trialkenylammonium, monoalkynylammonium, dialkynylammonium, monoalkanolammonium, dialkanolammonium, C5-C6-cycloalkylammonium, piperidinium, morpholinium, pyrrolidinium, or benzylammonium, moreover phosphonium ions, sulfonium ions, preferably tri(C1-C4-alkyl)sulfonium and sulfoxonium ions, preferably tri(C1-C4-alkyl)sulfoxonium.

Alkyl groups (either alone or as part of a larger group, such as alkoxy-, alkylsulfanyl-, alkylsulfinyl-, alkylsulfonyl-, alkylcarbonyl- or alkoxycarbonyl-) can be in the form of a straight or branched chain and are, for example, methyl, ethyl, 1-propyl, prop-2-yl, 1-butyl, but-2-yl, or 2-methyl-prop-2-yl. The alkyl group (either alone or as part of a larger group, such as alkoxy-, alkylsulfanyl-, alkylsulfinyl-, alkylsulfonyl-, alkylcarbonyl- or alkoxycarbonyl-), in each embodiment of the invention, is preferably C1-C3-alkyl, more preferably C1-C2-alkyl, especially methyl group. In the instance of alkoxy, examples are methoxy, ethoxy, propoxy, n-butoxy, isobutoxy and also their isomeric groups; preferably, independent of other embodiments, methoxy and ethoxy, especially methoxy.

Alkenyl groups can be in the form of straight or branched chains, and can be, where appropriate, of either the (E)- or (Z)-configuration. Examples are vinyl and allyl. The alkenyl group, in each embodiment of the invention, is preferably a C2-C3-alkenyl group, more preferably vinyl or allyl group.

Alkynyl groups can be in the form of straight or branched chains. Examples are ethynyl and propargyl. The alkynyl group, in each embodiment of the invention, is preferably a C2-C3-alkynyl group, more preferably propargyl group.

Halogen is fluorine, chlorine, bromine or iodine; halogen, in each embodiment of the invention, is fluorine, chlorine, or bromine; especially fluorine or chlorine.

Haloalkyl groups (either alone or as part of a larger group, such as haloalkoxy-, haloalkylsulfanyl-, haloalkylsulfinyl- or haloalkylsulfonyl-) are alkyl groups which are substituted by one or more of the same or different halogen atoms and are, for example, fluoromethyl, difluoromethyl, trifluoromethyl, chlorodifluoromethyl and 2,2,2-trifluoro-ethyl. The haloalkyl group (either alone or as part of a larger group, such as haloalkoxy-, haloalkylsulfanyl-, haloalkylsulfinyl- or haloalkylsulfonyl-), in each embodiment of the invention, is preferably trifluoromethyl. In instance of haloalkoxy, examples are fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2,2,2-trifluoroethoxy, 2-chloroethoxy and trifluoromethoxy Cycloalkyl groups are mono-cyclic and are, for example, cyclopropyl, cyclobutyl, cyclopentyl and cyclohexyl. The C3-C6-cycloalkyl group, in each embodiment of the invention, is preferably a C3-C5-cycloakyl, more preferably a C3-C4-cycloalkyl group, especially a C3-cycloalkyl group. Where a cycloalkyl moiety is said to be substituted, the cycloalkyl moiety is preferably substituted by one to four substituents, more preferably by one to three substituents, such as one or two substituents, especially by one substitutent.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl and tert-butoxycarbonyl; preferred are methoxycarbonyl, ethoxycarbonyl and isopropoxycarbonyl.

Alkylsulfanyl group is, for example, methylsulfanyl, ethylsulfanyl, propylsulfanyl, isopropylsulfanyl, n-butylsulfanyl, isobutylsulfanyl, sec-butylsulfanyl and tert-butylsulfanyl Examples of haloalkylsulfanyl are chloro- and/or fluoro-halogenated substituents thereof, such as difluoromethylsulfanyl, trifluoromethylsulfanyl, chlorodifluoromethylsulfanyl and 2,2,2-trifluoro-ethylsulfanyl.

Alkylsulfinyl is, for example, methylsulfinyl, ethylsulfinyl, propylsulfinyl, isopropylsulfinyl, n-butylsulfinyl, isobutylsulfinyl, sec-butylsulfinyl, and tert-butylsulfinyl. Examples of haloalkylsulfinyl are chloro- and/or fluoro-halogenated substituents thereof, such as difluoromethylsulfinyl, trifluoromethylsulfinyl, chlorodifluoromethylsulfinyl and 2,2,2-trifluoro-ethylsufhinyl.

Alkylsulfonyl group is, for example, methylsulfonyl, ethylsulfonyl, propylsulfonyl, isopropylsulfonyl, n-butylsulfonyl, isobutylsulfonyl, sec-butylsulfonyl and tert-butylsulfonyl. Examples of haloalkylsulfonyl are chloro- and/or fluoro-halogenated substituents thereof, such as difluoromethylsulfonyl, trifluoromethylsulfonyl, chlorodifluoromethylsulfonyl and 2,2,2-trifluoro-ethylsulfonyl.

Alkoxyalkyl is, for example, methoxymethyl, 2-methoxyethyl, ethoxymethyl, 2-ethoxyethyl, n-propoxymethyl, n-propoxy-2-ethyl, isopropoxymethyl and 1-isopropoxyethyl. The alkoxyalkyl group, in each embodiment of the invention, is preferably a C1-C4-alkoxy-C1-C4-alkyl, more preferably a C1-C2-alkoxy-methyl, such as methoxymethyl and ethoxymethyl groups.

Aryl groups (either alone or as part of a larger group, such as aryl-alkylene-) are aromatic ring systems which can be mono-, bi- or tricyclic. Examples of such rings include phenyl, naphthyl, anthracenyl, indenyl or phenanthrenyl. Preferred aryl groups are phenyl and naphthyl, phenyl being most preferred.

Examples of cycloalkylcarbonyl are cyclopropylcarbonyl, cyclobutylcarbonyl, cyclopentylcarbonyl and cyclohexylcarbonyl; preferred are cyclopropylcarbonyl and cyclobutylcarbonyl.

Examples of cycloalkoxycarbonyl are cyclopropyloxycarbonyl, cyclobutyloxycarbonyl, cyclopentyloxycarbonyl and cyclohexyloxycarbonyl; preferred are cyclopropyloxycarbonyl and cyclobutyloxycarbonyl.

The term "heteroaryl" refers to aromatic ring systems containing at least one heteroatom and consisting either of a single ring or of two fused rings. Preferably, single rings will contain up to 3 and bicyclic systems up to 5, heteroatoms, which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

It is possible that compounds of the formula I have further stereochemical centres, either at the carbon bearing R3 and R4, or when Y is CR12R13, or in one of the substituents. Further isomers are then possible. The invention covers all such isomers and mixtures thereof.

The compounds of the formula I may occur in different tautomeric forms. The invention covers all those tautomeric forms and mixtures thereof.

Preferably, A is an optionally substituted 5- or 6-membered heteroaromatic ring, which contains, preferably, an oxygen atom or one or two nitrogen atoms, such as furyl, pyridyl, pyrimidinyl, pyrazinyl, and pyridazinyl, in particular pyridyl, or A is preferably an optionally substituted phenyl. In an embodiment of any embodiment of A, there are 1 to 3, preferably 1 or 2, substitutents R6 on A.

More preferably A is a optionally substituted 6-membered heteroaromatic ring, which contains 1 or 2 nitrogen atoms (e.g. pyridyl, pyrimidinyl, pyrazinyl, and pyridazinyl, in particular pyridyl) or A is preferably an optionally substituted phenyl.

Preferred substituents (R6), independently of each other, and independently of the ring type, is selected from C1-C4-alkyl, C1-C4-haloalkyl (in particular di- and trifluoromethyl), C1-C4-haloalkoxy, cyano and halogen, in particular trifluoromethyl, fluoro and chloro.

Most preferably, A, independent of other embodiments, is pyridyl, pyrimidinyl, pyrazinyl, or phenyl, which can be unsubstituted or substituted by one or two of substituents R6, which can be selected independently from chloro, fluoro, trifluoromethyl, methyl, bromo, and cyano.

The preferable point or points of attachment of these substituents is ortho to the point of attachment of A to C(O)NR5.

Preferred examples of A, independent of other embodiments, are 2,6-difluorophenyl (A1); 3-chloro-2-pyrazinyl (A2); 3-trifluoromethyl-2-pyridyl (A3); 2-trifluoromethyl-3-pyridyl (A5); 2-trifluoromethyl-phenyl (A6); 2-chloro-3-pyridyl (A7); 3-methyl-2-pyridyl (A11); 2-methyl-3-pyridyl (A22); 3-methyl-2-pyrazinyl (A24); 3-bromo-2-pyrazinyl (A25); 3-trifluoromethyl-2-pyrazinyl (A26); and 2-cyanophenyl (A29).

Particularly preferred A independent of other embodiments, is selected from 3-chloro-2-pyrazinyl (A2); 3-trifluoromethyl-2-pyridyl (A3); 2-trifluoromethyl-3-pyridyl (A5); 2-trifluoromethyl-phenyl (A6); 2-chloro-3-pyridyl (A7); 3-methyl-2-pyrazinyl (A24); 3-bromo-2-pyrazinyl (A25); and 3-trifluoromethyl-2-pyrazinyl (A26).

Especially preferred A, independent of other embodiments, is selected from 3-chloro-2-pyrazinyl (A2); 3-trifluoromethyl-2-pyridyl (A3); 2-trifluoromethyl-3-pyridyl (A5); 2-trifluoromethyl-phenyl (A6); 2-chloro-3-pyridyl (A7); and 3-trifluoromethyl-2-pyrazinyl (A26); advantageously 3-chloro-2-pyrazinyl (A2); 2-trifluoromethyl-3-pyridyl (A5); 2-trifluoromethyl-phenyl (A6); and 3-trifluoromethyl-2-pyrazinyl (A26).

Preferably, Y is O or CR12R13, where R12 and R13 are, independently of each other, hydrogen, halogen, cyano, C1-C4-alkyl or C1-C4-haloalkyl. In an embodiment, independent of other embodiments, R12 and R13 are both hydrogen.

Preferably, R1, R2, R3 and R4 are, independently of each other, hydrogen, halogen, C1-C4-alkyl or C1-C4-haloalkyl. In an embodiment, independent of other embodiments, R1, R2, R3 and R4 are each hydrogen.

In an embodiment, when Y is CR12R13, five or six of R1, R2, R3, R4, R12 and R13 are hydrogen. In an preferred embodiment, Y is CR12R13, then R1, R3, R4, R12 and R13 are each hydrogen, and R2 is either cyano or C1-C4-alkoxy, such as methoxy.

In an embodiment, when Y is O, each of R1, R2, R3 and R4 are hydrogen.

Preferably, R5 is hydrogen.

B is phenyl substituted by substituents (R8). In an instance, there are 1 to 3 substitutents R8 on B. Preferably substituent R8, independently from each other, is selected from halogen, cyano, C1-C4-alkyl, C1-C4-alkoxy, C1-C4-haloalkyl, C1-C4-haloalkoxy, C1-C4-alkylthio, C1-C4-haloalkylthio, cyclopropyl, cyclobutyl, cyclopentyl, C1-C4-haloalkyl-C3-C6-cycloalkyl, phenyl, phenoxy, cyclopentyloxy, allyl, propargyl, allyloxy, propargyloxy, C1-C4-alkylsulfoxide, C1-C4-haloalkylsulfoxide, C1-C4-alkylsulfonyl, C1-C4-haloalkylsulfonyl, C1-C4-alkylsulfonylamino, propargylsulfonylamino, cyclopropylsulfonamino, cyclobutylsulfonamino, cyclopentylsulfonamino, phenylsulfonamino, pyridylsulfonamino, pyridyl, imidazolyl, pyridyloxy, phenylcarbonyl, phenoxycarbonyl, phenylcarbonyloxy, pyridylcarbonyl, pyridyloxycarbonyl, pyridylcarbonyloxy, C1-C4-alkoxycarbonyl, C1-C4-alkylcarbonyloxy, cyclopentyloxycarbonyl, allyloxycarbonyl, propargyloxycarbonyl, allylcarbonyloxy, propargylcarbonyloxy, C1-C4-alkylamino, cyclopentylamino, phenylaminosulfonyl, C1-C4-alkylaminosulfonyl, cyclopentylaminosulfonyl, pyridylaminosulfonyl, allylaminosulfonyl, propargylaminosulfonyl, phenylamino, pyridylamino, allylamino, propargylamino, phenylaminocarbonyl, pyridylaminocarbonyl, cyclopentylaminocarbonyl, phenylcarbonylamino, pyridylcarbonylamino, allylcarbonylamino and propargylcarbonylamino, where these substituents, independent of each other, can be unsubstituted, or, where allowable, can be further substituted by one or more substituents (R10). Substitutent R10, independently selected from each other, is preferably selected from C1-C4-alkyl, C1-C4-alkoxy, C1-C4-haloalkyl, C1-C4-alkylthio and halogen.

In an embodiment, independent of other embodiments, B is a phenyl substituted 1 to 3 substituents, independently selected from halogen, cyano, C1-C4-haloalkyl, C1-C4-haloalkoxy, and C3-C6-cycloalkyl. In a preferred embodiment, the substitutents are independently selected from bromo, chloro, fluoro, trifluoromethyl, difluoromethoxy, trifluoromethoxy and cyclopropyl.

In a group of preferred compounds of the formula I, B is a phenyl, substituted by 1 to 3 substituents, independently selected from halogen, cyclopropyl, C1-C4-haloalkylcyclopropyl, C1-C4-haloalkyl and C1-C4-haloalkoxy, A is a phenyl, furyl, pyridyl, pyrimidinyl, pyrazinyl or pyridazinyl, which rings, independently of each other, are unsubstituted or substituted by 1 to 3 substituents, independently selected, from C1-C4-alkyl, C1-C4-haloalkyl, C1-C4-alkoxy, C1-C4-haloalkoxy, cyano and halogen, Y is O or CH2, and R1, R2, R3, R4 and R5 are hydrogen. In this group of compounds of formula I, B is especially a phenyl substituted by 1 to 3 substituents, independently selected from fluoro, chloro, bromo, trifluoromethyl and trifluoromethoxy. In this group of compounds of formula I, A is especially a phenyl, pyridyl, pyrazinyl or pyrimidinyl, which rings are, independently of each other, unsubstituted or substituted by 1 to 3 substituents, independently selected from fluoro, methyl and trifluoromethyl.

In another group of preferred compounds of the formula I, B is a phenyl substituted by 1 to 3 substituents, independently selected from fluoro, chloro, trifluoromethyl, cyclopropyl, trifluoromethylcyclopropyl, difluoromethoxy or trifluoromethoxy, A is a phenyl, pyridyl or pyrazinyl, which rings, independent I of each other, are unsubstituted or substituted by 1 to 3 substituents, independently selected from chloro, bromo, fluoro, methyl, cyano, and trifluoromethyl, Y is O or CH2, and R1, R2, R3, R4 and R5 are hydrogen. More preferably in this group of compounds of formula I, B is especially a phenyl substituted by 1 to 3 substituents, independently from fluoro, chloro, difluoromethoxy or trifluoromethoxy, A is especially a phenyl, pyrazinyl or pyridyl, which rings, independently of each other, are substituted by 1 to 3 substituents, independently selected from chloro, fluoro, methyl and trifluoromethyl.

In an especially preferred group of compound of formula I, B is a phenyl substituted by 1 to 3 substituents, independently selected, from halogen, C1-C4-haloalkyl, and C1-C4-haloalkoxy; A is phenyl, pyridyl or pyrazinyl, which rings, independently of each other, are mono-substituted by a halogen or C1-C4-haloalkyl; Y is O or CH2; and R1, R2, R3, R4 and R5 are hydrogen. More preferably in this group of compounds of formula I, B is especially a phenyl substituted by 1 to 2 substituents, independently selected, from fluoro, chloro, trifluoromethyl, difluoromethoxy and trifluoromethoxy; A is especially a phenyl, pyrazinyl or pyridyl, which rings are mono-substituted by substituents from chloro, fluoro or trifluoromethyl.

In a particularly preferred embodiment, a compound of formula I is where Y is CH2; B is mono or di-halogen substituted phenyl; R1 to R5 are each hydrogen and A is selected from phenyl, pyrazinyl or pyridyl, each of which is mono- or disubstituted, independently of each other, by substituents independently selected from halogen and C1-C4-haloalkyl, preferably A is mono-substituted.

Compounds of formula I may be prepared by reacting a compound of formula II

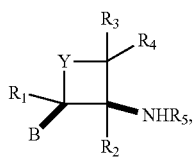

in which B, Y, $R_1$, $R_2$, $R_3$, $R_4$ and $R_5$ are as defined under formula I; with an acylating agent of formula III

A-C(=O)—R*      (III), in which A is as defined under formula I, and R* is halogen, hydroxy or $C_{1-6}$ alkoxy, preferably chloro, in the presence of a base, such as triethylamine, Hunig base, sodium bicarbonate, sodium carbonate, potassium carbonate, pyridine or quinoline, but preferably triethylamine, and generally in a solvent, such as diethylether, TBME, THF, dichloromethane, chloroform, DMF or NMP, for between 10 minutes and 48 hours, preferably 12 to 24 hours, and between 0° C. and reflux, preferably 20 to 25° C.

When R* is hydroxyl, a coupling agent, such as benzotriazol-1-yloxytris(dimethylamino) phosphoniumhexafluorophosphate, bis-(2-oxo-3-oxazolidinyl)-phosphinic acid chloride (BOP-Cl), N,N'-dicyclohexylcarbodiimide (DCC) or 1,1'-carbonyl-diimidazole (CD), may be used.

Compounds of the formula IIc in which B is as defined under formula I, Y is CH2 and R1, R2, R3 and R4 is H can be prepared from the ketone XVIII. This can be done by conversion to the oxime XIX and reduction. D. E. Nichols et al. (J. Med. Chem. 1984, 27, 1108-11) describe methods for this reduction. Certain methods may yield trans isomers as side-products.

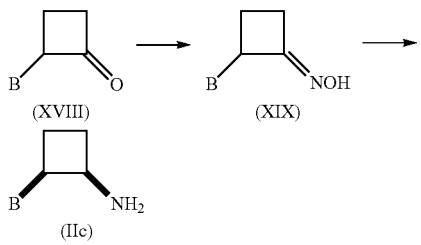

Compounds of the formula Ie can be made by 2+2 cycload-dition of aldehydes of the formula (VIII) and enamides of the formula (Va). This can be performed with the assistance of UV radiation as described by Bach et al. (Journal of Organic Chemistry (1999), 64(4), 1265-1273). They may be accompanied by their trans isomers

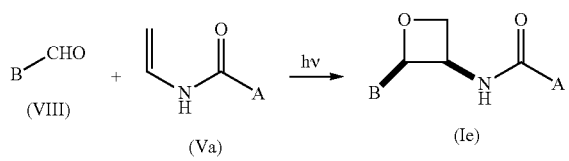

For preparing all further compounds of the formula I functionalized according to the definitions of A, B, $R_1$, $R_2$, $R_3$, $R_4$, $R_5$ and $R_{12}$ and $R_{13}$ there are a large number of suitable known standard methods, such as alkylation, halogenation, acylation, amidation, oximation, oxidation and reduction. The choice of the preparation methods which are suitable are depending on the properties (reactivity) of the substituents in the intermediates.

These reactions can be conveniently performed in a solvent.

These reactions can be conveniently performed at various temperatures.

These reactions can be conveniently performed in an inert atmosphere.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula (I) can be converted in a manner known per se into another compound of formula (I) by replacing one or more substituents of the starting compound of formula (I) in the customary manner by (an) other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula (I) can be prepared in a manner known per se. Thus, for example, acid addition salts of compounds of formula (I) are obtained by treatment with a suitable acid or a suitable ion exchanger reagent and salts with bases are obtained by treatment with a suitable base or with a suitable ion exchanger reagent. A salt is chosen depending on its tolerances for compound's use, such as agricultural or physiological tolerance.

Salts of compounds of formula (I) can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula (I) can be converted in a manner known per se into other salts of compounds of formula (I), acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula (I), which have salt-forming properties can be obtained in free form or in the form of salts.

Diastereomer mixtures or racemate mixtures of compounds of formula (I), in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphoric, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula (I) with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615 or C. White, Science, vol 318, p. 783, 2007.

It can be advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula (I) and, where appropriate, the tautomers thereof, in each case in free form or in salt form, can, if appropriate, also be obtained in the form of hydrates and/or include other solvents, for example those which may have been used for the crystallization of compounds which are present in solid form.

The invention is further directed to intermediate compounds having formulae (II), and (XIXa), which may be used in the preparation of the compounds of formula (I).

Accordingly, the present invention makes available a compound of formula (II)

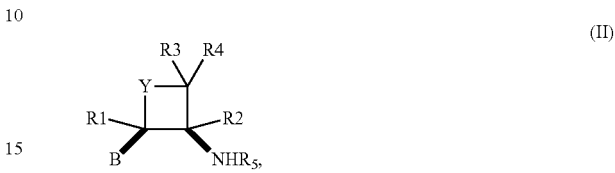

(II)

wherein
Y is O, C=O, or CR12R13;
R1, R2, R3, R4, R12 and R13, independently of each other, are hydrogen, halogen, cyano, C1-C4-alkyl or C1-C4-haloalkyl,
R5 is hydrogen, methoxy or hydroxyl,
B is phenyl substituted by one or more R8,
R8 is, independently of each other, halogen, cyano or a group -L-R9, where each L is independently of each other a bond, —O—, —OC(O)—, —NR7-, —NR7CO—, —NR7S(O)n-, —S(O)n-, —S(O)nNR7-, —COO— or CONR7-,
n is 0, 1 or 2,
R7 is hydrogen, C1-C4-alkyl, C1-C4-haloalkyl, benzyl or phenyl, where benzyl and phenyl is unsubstituted or substituted with halogen, cyano, C1-C4-alkyl or C1-C4-haloalkyl,
R9 is, independently of each other, C1-C6-alkyl, which is unsubstituted or substituted by one or more R10, C3-C6-cycloalkyl, which is unsubstituted or substituted by one or more R10, C6-C14-bicycloalkyl, which is unsubstituted or substituted by one or more R10, C2-C6-alkenyl, which is unsubstituted or substituted by one or more R10, C2-C6-alkynyl, which is unsubstituted or substituted by one or more R10, phenyl, which is unsubstituted or substituted by R10, or heteroaryl, which is unsubstituted or substituted by one or more R10,
R10 is, independently of each other, halogen, cyano, C1-C4-alkyl, C1-C4-haloalkyl, C1-C4-alkoxy, C1-C4-haloalkoxy, C1-C4-alkylthio, C1-C4-haloalkylthio, C3-C6-alkenyloxy, or C3-C6-alkynyloxy, provided the B and A-CO—NR5 are cis to each other on the four-membered ring, where the compound of the formula

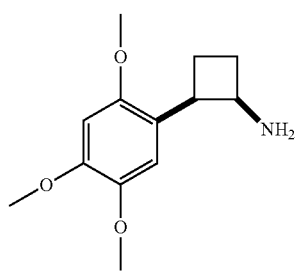

is excluded.

In preferred embodiment, any preferred substitutent of formula (I) in connection with each of B, Y, R1, R2, R3, R4, and R5 is also a preferred substituent, independent of formula (I), for formula (II) in context of B, Y, R1, R2, R3, R4, and R5 respectively.

Especially Y is CH2, R1 to R5 are each hydrogen and B is a phenyl, substituted by 1 to 3 substituents, independently selected from halogen, cyclopropyl, C1-C4-haloalkylcyclopropyl, C1-C4-haloalkyl and C1-C4-haloalkoxy.

In particular embodiment, Y is CH2, R1 to R5 are each hydrogen and B is a phenyl substituted by 1 to 3 substituents, independently selected from fluoro, chloro, trifluoromethyl, cyclopropyl, trifluoromethylcyclopropyl and trifluoromethoxy.

In a particularly preferred embodiment, Y is CH2, R1 to R5 are each hydrogen and B is a mono or di-halogen substituted phenyl.

The present invention additionally makes available a compound of formula (XIXa)

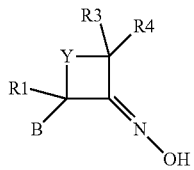
(XIXa)

wherein
Y is O, C=O, or CR12R13;
R1, R3, and R4 independently of each other, are hydrogen, halogen, cyano, C1-C4-alkyl or C1-C4-haloalkyl,
B is phenyl substituted by one or more R8,
R8 is, independently of each other, halogen, cyano or a group -L-R9, where each L is independently of each other a bond, —O—, —OC(O)—, —NR7-, —NR7CO—, —NR7S(O)n-, —S(O)n-, —S(O)nNR7-, —COO— or CONR7-,
n is 0, 1 or 2,
R7 is hydrogen, C1-C4-alkyl, C1-C4-haloalkyl, benzyl or phenyl, where benzyl and phenyl is unsubstituted or substituted with halogen, cyano, C1-C4-alkyl or C1-C4-haloalkyl,
R9 is, independently of each other, C1-C6-alkyl, which is unsubstituted or substituted by one or more R10, C3-C6-cycloalkyl, which is unsubstituted or substituted by one or more R10, C6-C14-bicycloalkyl, which is unsubstituted or substituted by one or more R10, C2-C6-alkenyl, which is unsubstituted or substituted by one or more R10, C2-C6-alkynyl, which is unsubstituted or substituted by one or more R10, phenyl, which is unsubstituted or substituted by R10, or heteroaryl, which is unsubstituted or substituted by one or more R10,
R10 is, independently of each other, halogen, cyano, C1-C4-alkyl, C1-C4-haloalkyl, C1-C4-alkoxy, C1-C4-haloalkoxy, C1-C4-alkylthio, C1-C4-haloalkylthio, C3-C6-alkenyloxy, or C3-C6-alkynyloxy, provided the B and A-CO—NR5 are cis to each other on the four-membered ring; where the compounds of the formulae

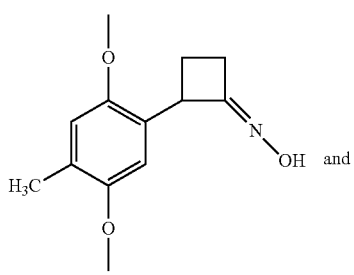 and

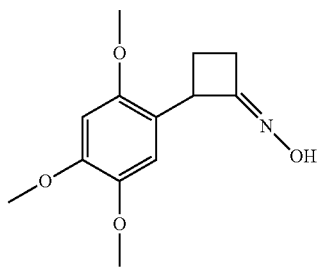

are excluded.

In preferred embodiment, any preferred substitutent of formula (I) in connection with each of B, Y, R1, R3, and R4, is also a preferred substituent, independent of formula (I), for formula (XIXa) in context of B, Y, R1, R3, and R4 respectively.

Especially Y is CH2, R1, R3 and R4 are each hydrogen and B is a phenyl, substituted by 1 to 3 substituents, independently selected from halogen, cyclopropyl, C1-C4-haloalkylcyclopropyl, C1-C4-haloalkyl and C1-C4-haloalkoxy.

In particular embodiment, Y is CH2, R1, R3 and R4 are each hydrogen and B is a phenyl substituted by 1 to 3 substituents, independently selected from fluoro, chloro, trifluoromethyl, cyclopropyl, trifluoromethylcyclopropyl and trifluoromethoxy.

In a particularly preferred embodiment, Y is CH2, R1, R3 and R4 are each hydrogen and B is a mono or di-halogen substituted phenyl.

Tables 1 to 33: Compounds of Formula IA

The invention is further illustrated by making available the following individual compounds of formula (IA) listed below in Tables 1 to 33.

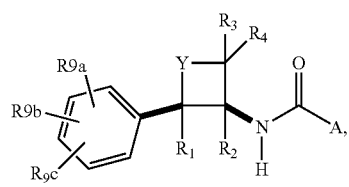
(IA)

Each of Tables 1 to 33, which follow the Table Y below, make available 163 compounds of the formula (IA) in which Y, $R_1$, $R_2$, $R_3$, $R_4$, $R_{9a}$, $R_{9b}$ and $R_{9c}$ are the substituents defined in Table Y and A is the substituent defined in the relevant Table 1 to 33. Thus Table 1 individualizes 163 compounds of formula (IA) wherein for each row of Table Y, the A substituent is as defined in Table 1; similarly, Table 2 individualizes 163 compounds of formula (IA) wherein for each row of Table Y, the A substituent is as defined in Table 2; and so on for Tables 3 to 33.

TABLE Y

| Compound No. | Y | R₁ | R₂ | R₃ | R₄ | R₉ₐ | R₉ᵦ | R₉c |
|---|---|---|---|---|---|---|---|---|
| Y.001 | CH₂ | H | H | H | H | 4-Cl | H | H |
| Y.002 | CH₂ | Me | H | H | H | 4-Cl | H | H |
| Y.003 | CH₂ | nPr | H | H | H | 4-Cl | H | H |
| Y.004 | CH₂ | F | H | H | H | 4-Cl | H | H |
| Y.005 | CH₂ | CN | H | H | H | 4-Cl | H | H |
| Y.006 | CH₂ | CF₃ | H | H | H | 4-Cl | H | H |
| Y.007 | CH₂ | H | Me | H | H | 4-Cl | H | H |
| Y.008 | CH₂ | H | nPr | H | H | 4-Cl | H | H |
| Y.009 | CH₂ | H | F | H | H | 4-Cl | H | H |
| Y.010 | CH₂ | H | CN | H | H | 4-Cl | H | H |
| Y.011 | CH₂ | H | CF₃ | H | H | 4-Cl | H | H |
| Y.012 | CH₂ | H | Me | Me | H | 4-Cl | H | H |
| Y.013 | CH₂ | H | nPr | nPr | H | 4-Cl | H | H |
| Y.014 | CH₂ | H | F | F | H | 4-Cl | H | H |
| Y.015 | CH₂ | H | CN | CN | H | 4-Cl | H | H |
| Y.016 | CH₂ | H | CF₃ | CF₃ | H | 4-Cl | H | H |
| Y.017 | CH₂ | H | H | H | Me | 4-Cl | H | H |
| Y.018 | CH₂ | H | H | H | nPr | 4-Cl | H | H |
| Y.019 | CH₂ | H | H | H | F | 4-Cl | H | H |
| Y.020 | CH₂ | H | H | H | CN | 4-Cl | H | H |
| Y.021 | CH₂ | H | H | H | CF₃ | 4-Cl | H | H |
| Y.022 | CHMe | H | H | H | H | 4-Cl | H | H |
| Y.023 | CHnPr | H | H | H | H | 4-Cl | H | H |
| Y.024 | CHF | H | H | H | H | 4-Cl | H | H |
| Y.025 | CHCN | H | H | H | H | 4-Cl | H | H |
| Y.026 | CHCF₃ | H | H | H | H | 4-Cl | H | H |
| Y.027 | CMe₂ | H | H | H | H | 4-Cl | H | H |
| Y.028 | O | H | H | H | H | 4-Cl | H | H |
| Y.029 | CH₂ | H | H | H | H | 2-Cl | H | H |
| Y.030 | CH₂ | H | H | H | H | 4-OBn | H | H |
| Y.031 | CH₂ | H | H | H | H | 4-F | H | H |
| Y.032 | CH₂ | H | H | H | H | 4-OCHF₂ | H | H |
| Y.033 | CH₂ | H | H | H | H | 2-Cl | 4-Br | H |
| Y.034 | CH₂ | H | H | H | H | 2-Cl | 4-Cl | H |
| Y.035 | CH₂ | H | H | H | H | 2-F | 4-Cl | H |
| Y.036 | CH₂ | H | H | H | H | 4-CF3 | H | H |
| Y.037 | CH₂ | H | H | H | H | 3-F | 4-Cl | H |
| Y.038 | CH₂ | H | H | H | H | 4-OCF₃ | H | H |
| Y.039 | CH₂ | H | H | H | H | 4-Br | H | H |
| Y.040 | CH₂ | H | H | H | H | 4-CN | H | H |
| Y.041 | CH₂ | H | H | H | H | 2-CF₃ | 4-F | H |
| Y.042 | CH₂ | H | H | H | H | 2-Br | 4-F | H |
| Y.043 | CH₂ | H | H | H | H | 4-SMe | H | H |
| Y.044 | CH₂ | H | H | H | H | 4-cPr | H | H |
| Y.045 | CH₂ | H | H | H | H | 4-S(O)Me | H | H |
| Y.046 | CH₂ | H | H | H | H | 4-S(O)2Me | H | H |
| Y.047 | CH₂ | H | H | H | H | 2-F | 4-F | H |
| Y.048 | CH₂ | H | H | H | H | 2-Cl | 4-F | H |
| Y.049 | CH₂ | H | H | H | H | 4-(imidazol-1-yl) | H | H |
| Y.050 | CH₂ | H | H | H | H | 2-F | 4-F | 6-F |
| Y.051 | CH₂ | H | H | H | H | 4-methyl | H | H |
| Y.052 | CH₂ | H | H | H | H | 4-cyclopentyl | H | H |
| Y.053 | CH₂ | H | H | H | H | 4-allyl | H | H |
| Y.054 | CH₂ | H | H | H | H | 4-propargyl | H | H |
| Y.055 | CH₂ | H | H | H | H | 4-(4-chloro-phenyl) | H | H |
| Y.056 | CH₂ | H | H | H | H | 4-(3,5-dichloro-pyrid-2yl) | H | H |
| Y.057 | CH₂ | H | H | H | H | 4-methoxy | H | H |
| Y.058 | CH₂ | H | H | H | H | 4-cyclopentyl-oxy | H | H |
| Y.059 | CH₂ | H | H | H | H | 4-allyloxy | H | H |
| Y.060 | CH₂ | H | H | H | H | 4-propargyloxy | H | H |
| Y.061 | CH₂ | H | H | H | H | 4-(4-chloro-phenyl)oxy | H | H |
| Y.062 | CH₂ | H | H | H | H | 4-(3,5-dichloro-pyrid-2yl)oxy | H | H |
| Y.063 | CH₂ | H | H | H | H | 4-methoxy-carbonyl | H | H |
| Y.064 | CH₂ | H | H | H | H | 4-cyclopentyl-oxycarbonyl | H | H |
| Y.065 | CH₂ | H | H | H | H | 4-allyl-oxycarbonyl | H | H |
| Y.066 | CH₂ | H | H | H | H | 4-propargyl-oxycarbonyl | H | H |

TABLE Y-continued

| Compound No. | Y | $R_1$ | $R_2$ | $R_3$ | $R_4$ | $R_{9a}$ | $R_{9b}$ | $R_{9c}$ |
|---|---|---|---|---|---|---|---|---|
| Y.067 | $CH_2$ | H | H | H | H | 4-(4-chloro-phenyl)-oxycarbonyl | H | H |
| Y.068 | $CH_2$ | H | H | H | H | 4-(3,5-dichloro-pyrid-2yl)-oxycarbonyl | H | H |
| Y.069 | $CH_2$ | H | H | H | H | 4-methylamino | H | H |
| Y.070 | $CH_2$ | H | H | H | H | 4-cyclopentylamino | H | H |
| Y.071 | $CH_2$ | H | H | H | H | 4-allylanimo | H | H |
| Y.072 | $CH_2$ | H | H | H | H | 4-propargylamino | H | H |
| Y.073 | $CH_2$ | H | H | H | H | 4-(4-chloro-phenyl)-amino | H | H |
| Y.074 | $CH_2$ | H | H | H | H | 4-(3,5-dichloro-pyrid-2yl)-amino | H | H |
| Y.075 | $CH_2$ | H | H | H | H | 4-methyl-N-phenylamino | H | H |
| Y.076 | $CH_2$ | H | H | H | H | 4-cyclopentyl-N-phenylamino | H | H |
| Y.077 | $CH_2$ | H | H | H | H | 4-allyl-N-phenylamino | H | H |
| Y.078 | $CH_2$ | H | H | H | H | 4-propargyl-N-phenylamino | H | H |
| Y.079 | $CH_2$ | H | H | H | H | 4-(4-chloro-phenyl)-N-phenylamino | H | H |
| Y.080 | $CH_2$ | H | H | H | H | 4-(3,5-dichloro-pyrid-2yl)-N-phenylamino | H | H |
| Y.081 | $CH_2$ | H | H | H | H | 4-methyl-N-methylamino | H | H |
| Y.082 | $CH_2$ | H | H | H | H | 4-cyclopentyl-N-methylamino | H | H |
| Y.083 | $CH_2$ | H | H | H | H | 4-allyl-N-methylamino | H | H |
| Y.084 | $CH_2$ | H | H | H | H | 4-propargyl-N-methylamino | H | H |
| Y.085 | $CH_2$ | H | H | H | H | 4-(4-chloro-phenyl)-N-methylamino | H | H |
| Y.086 | $CH_2$ | H | H | H | H | 4-(3,5-dichloro-pyrid-2yl)-N-methylamino | H | H |
| Y.087 | $CH_2$ | H | H | H | H | 4-methyl-aminocarbonyl | H | H |
| Y.088 | $CH_2$ | H | H | H | H | 4-cyclopentyl-aminocarbonyl | H | H |
| Y.089 | $CH_2$ | H | H | H | H | 4-allyl-aminocarbonyl | H | H |
| Y.090 | $CH_2$ | H | H | H | H | 4-propargyl-aminocarbonyl | H | H |
| Y.091 | $CH_2$ | H | H | H | H | 4-(4-chloro-phenyl)-aminocarbonyl | H | H |
| Y.092 | $CH_2$ | H | H | H | H | 4-(3,5-dichloro-pyrid-2yl)-aminocarbonyl | H | H |
| Y.093 | $CH_2$ | H | H | H | H | 4-methyl-N-methylaminocarbonyl | H | H |
| Y.094 | $CH_2$ | H | H | H | H | 4-cyclopentyl-N-methylamino-carbonyl | H | H |

TABLE Y-continued

| Compound No. | Y | $R_1$ | $R_2$ | $R_3$ | $R_4$ | $R_{9a}$ | $R_{9b}$ | $R_{9c}$ |
|---|---|---|---|---|---|---|---|---|
| Y.095 | $CH_2$ | H | H | H | H | 4-allyl-N-methylaminocarbonyl | H | H |
| Y.096 | $CH_2$ | H | H | H | H | 4-propargyl-N-methylaminocarbonyl | H | H |
| Y.097 | $CH_2$ | H | H | H | H | 4-(4-chlorophenyl)-N-methylaminocarbonyl | H | H |
| Y.098 | $CH_2$ | H | H | H | H | 4-(3,5-dichloro-pyrid-2yl)-N-methylaminocarbonyl | H | H |
| Y.099 | $CH_2$ | H | H | H | H | 4-methyl aminosulfonyl | H | H |
| Y.100 | $CH_2$ | H | H | H | H | 4-cyclopentyl aminosulfonyl | H | H |
| Y.101 | $CH_2$ | H | H | H | H | 4-allyl aminosulfonyl | H | H |
| Y.102 | $CH_2$ | H | H | H | H | 4-propargyl aminosulfonyl | H | H |
| Y.103 | $CH_2$ | H | H | H | H | 4-(4-chlorophenyl) aminosulfonyl | H | H |
| Y.104 | $CH_2$ | H | H | H | H | 4-(3,5-dichloro-pyrid-2yl) aminosulfonyl | H | H |
| Y.105 | $CH_2$ | H | H | H | H | 4-methyl sulfonyl | H | H |
| Y.106 | $CH_2$ | H | H | H | H | 4-cyclopentyl sulfonyl | H | H |
| Y.107 | $CH_2$ | H | H | H | H | 4-allyl sulfonyl | H | H |
| Y.108 | $CH_2$ | H | H | H | H | 4-propargyl sulfonyl | H | H |
| Y.109 | $CH_2$ | H | H | H | H | 4-(4-chlorophenyl) sulfonyl | H | H |
| Y.110 | $CH_2$ | H | H | H | H | 4-(3,5-dichloro-pyrid-2yl) sulfonyl | H | H |
| Y.111 | $CH_2$ | H | H | H | H | 4-methyl sulfonylamino | H | H |
| Y.112 | $CH_2$ | H | H | H | H | 4-cyclopentyl sulfonylamino | H | H |
| Y.113 | $CH_2$ | H | H | H | H | 4-allyl sulfonylamino | H | H |
| Y.114 | $CH_2$ | H | H | H | H | 4-propargyl sulfonylamino | H | H |
| Y.115 | $CH_2$ | H | H | H | H | 4-(4-chlorophenyl) sulfonylamino | H | H |
| Y.116 | $CH_2$ | H | H | H | H | 4-(3,5-dichloro-pyrid-2yl) sulfonylamino | H | H |
| Y.117 | $CH_2$ | H | H | H | H | 4-methyl sulfonyl-N-methylamino | H | H |
| Y.118 | $CH_2$ | H | H | H | H | 4-cyclopentyl sulfonyl-N-methylamino | H | H |
| Y.119 | $CH_2$ | H | H | H | H | 4-allyl sulfonyl-N-methylamino | H | H |
| Y.120 | $CH_2$ | H | H | H | H | 4-propargyl sulfonyl-N-methylamino | H | H |
| Y.121 | $CH_2$ | H | H | H | H | 4-(4-chlorophenyl) sulfonyl-N-methylamino | H | H |

TABLE Y-continued

| Compound No. | Y | $R_1$ | $R_2$ | $R_3$ | $R_4$ | $R_{9a}$ | $R_{9b}$ | $R_{9c}$ |
|---|---|---|---|---|---|---|---|---|
| Y.122 | $CH_2$ | H | H | H | H | 4-(3,5-dichloro-pyrid-2yl) sulfonyl-N-methylamino | H | H |
| Y.123 | $CH_2$ | H | H | H | H | 4-acetoxy | H | H |
| Y.124 | $CH_2$ | H | H | H | H | 4-cyclopentyl-carbonyloxy | H | H |
| Y.125 | $CH_2$ | H | H | H | H | 4-allylcarbonyloxy | H | H |
| Y.126 | $CH_2$ | H | H | H | H | 4-propargyl-carbonyloxy | H | H |
| Y.127 | $CH_2$ | H | H | H | H | 4-(4-chloro-phenyl) carbonyloxy | H | H |
| Y.128 | $CH_2$ | H | H | H | H | 4-(3,5-dichloro-pyrid-2yl) carbonyloxy | H | H |
| Y.129 | $CH_2$ | H | H | H | H | 4-acetamido | H | H |
| Y.130 | $CH_2$ | H | H | H | H | 4-cyclopentylcarbonylamino | H | H |
| Y.131 | $CH_2$ | H | H | H | H | 4-allylcarbonyl-amino | H | H |
| Y.132 | $CH_2$ | H | H | H | H | 4-propargylcarbonylamino | H | H |
| Y.133 | $CH_2$ | H | H | H | H | 4-(4-chloro-phenyl) carbonylamino | H | H |
| Y.134 | $CH_2$ | H | H | H | H | 4-(3,5-dichloro-pyrid-2yl) carbonylamino | H | H |
| Y.136 | O | H | H | H | H | 2-Cl | H | H |
| Y.137 | O | H | H | H | H | 4-OBn | H | H |
| Y.138 | O | H | H | H | H | 4-F | H | H |
| Y.139 | O | H | H | H | H | 4-$OCHF_2$ | H | H |
| Y.140 | O | H | H | H | H | 2-Cl | 4-Br | H |
| Y.141 | O | H | H | H | H | 2-Cl | 4-Cl | H |
| Y.142 | O | H | H | H | H | 2-F | 4-Cl | H |
| Y.143 | O | H | H | H | H | 4-$CF_3$ | H | H |
| Y.144 | O | H | H | H | H | 3-F | 4-Cl | H |
| Y.145 | O | H | H | H | H | 4-$OCF_3$ | H | H |
| Y.146 | O | H | H | H | H | 4-Br | H | H |
| Y.147 | O | H | H | H | H | 4-CN | H | H |
| Y.148 | O | H | H | H | H | 2-$CF_3$ | 4-F | H |
| Y.149 | O | H | H | H | H | 2-Br | 4-F | H |
| Y.150 | O | H | H | H | H | 4-SMe | H | H |
| Y.151 | O | H | H | H | H | 4-cPr | H | H |
| Y.152 | O | H | H | H | H | 4-S(O)Me | H | H |
| Y.153 | O | H | H | H | H | 4-S(O)2Me | H | H |
| Y.154 | O | H | H | H | H | 2-F | 4-F | H |
| Y.155 | O | H | H | H | H | 2-Cl | 4-F | H |
| Y.156 | O | H | H | H | H | 4-(imidazol-1-yl) | H | H |
| Y.157 | O | H | H | H | H | 2-F | 4-F | 6-F |
| Y.158 | O | H | H | H | H | 4-methyl | H | H |
| Y.159 | O | H | H | H | H | 4-cyclopentyl | H | H |
| Y.160 | O | H | H | H | H | 4-allyl | H | H |
| Y.161 | O | H | H | H | H | 4-propargyl | H | H |
| Y.162 | O | H | H | H | H | 4-(4-chloro-phenyl) | H | H |
| Y.163 | O | H | H | H | H | 4-(3,5-dichloro-pyrid-2yl) | H | H |

Table 1 provides 163 compounds of formula (IA), wherein A is

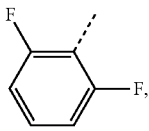
(A1)

(2,6-difluorophenyl) wherein the broken line indicates the point of attachment of the group A to the amide group, and Y, $R_1$, $R_2$, $R_3$, $R_4$, $R_{9a}$, $R_{9b}$ and $R_{9c}$ are as defined in each row of Table Y. For example, compound 1.001 has the following structure:

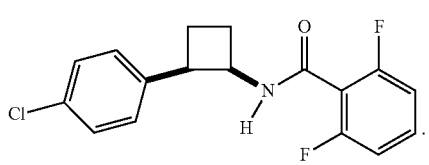
(1.001)

Table 2 provides 163 compounds of formula (IA) wherein A is 3-chloro-2-pyrazinyl (A2) and Y, $R_1$, $R_2$, $R_3$, $R_4$, $R_{9a}$, $R_{9b}$ and $R_{9c}$ are as defined in each row of Table Y.

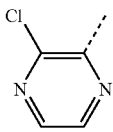

Table 3 provides 163 compounds of formula (IA) wherein A is 3-trifluoromethyl-2-pyridyl (A3) and Y, $R_1$, $R_2$, $R_3$, $R_4$, $R_{9a}$, $R_{9b}$ and $R_{9c}$ are as defined in each row of Table Y.

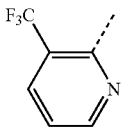

Table 4 provides 163 compounds of formula (IA) wherein A is 3-chloro-2-pyridyl (A4) and Y, $R_1$, $R_2$, $R_3$, $R_4$, $R_{9a}$, $R_{9b}$ and $R_{9c}$ are as defined in each row of Table Y.

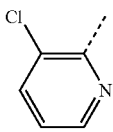

Table 5 provides 163 compounds of formula (IA) wherein A is 2-trifluoromethyl-3-pyridyl (A5) and Y, $R_1$, $R_2$, $R_3$, $R_4$, $R_{9a}$, $R_{9b}$ and $R_{9c}$ are as defined in each row of Table Y.

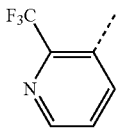

Table 6 provides 163 compounds of formula (IA) wherein A is 2-trifluoromethyl-phenyl (A6) and Y, $R_1$, $R_2$, $R_3$, $R_4$, $R_{9a}$, $R_{9b}$ and $R_{9c}$ are as defined in each row of Table Y.

Table 7 provides 163 compounds of formula (IA) wherein A is 2-chloro-3-pyridyl (A7) and Y, $R_1$, $R_2$, $R_3$, $R_4$, $R_{9a}$, $R_{9b}$ and $R_{9c}$ are as defined in each row of Table Y.

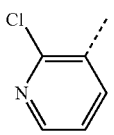

Table 8 provides 163 compounds of formula (IA) wherein A is 2-fluoro-6-trifluoromethyl-phenyl (A8) and Y, $R_1$, $R_2$, $R_3$, $R_4$, $R_{9a}$, $R_{9b}$ and $R_{9c}$ are as defined in each row of Table Y.

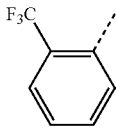

Table 9 provides 163 compounds of formula (IA) wherein A is 2-tolyl (A9) and Y, $R_1$, $R_2$, $R_3$, $R_4$, $R_{9a}$, $R_{9b}$ and $R_{9c}$ are as defined in each row of Table Y.

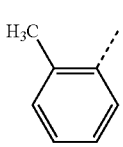

Table 10 provides 163 compounds of formula (IA) wherein A is 2-pyrimidinyl (A10) and Y, $R_1$, $R_2$, $R_3$, $R_4$, $R_{9a}$, $R_{9b}$ and $R_{9c}$ are as defined in each row of Table Y.

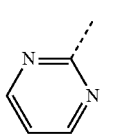

Table 11 provides 163 compounds of formula (IA) wherein A is 3-methyl-2-pyridyl (A11) and Y, $R_1$, $R_2$, $R_3$, $R_4$, $R_{9a}$, $R_{9b}$ and $R_{9c}$ are as defined in each row of Table Y.

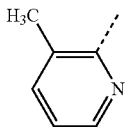

Table 12 provides 163 compounds of formula (IA) wherein A is 2-fluorophenyl (A12) and Y, $R_1$, $R_2$, $R_3$, $R_4$, $R_{9a}$, $R_{9b}$ and $R_{9c}$ are as defined in each row of Table Y.

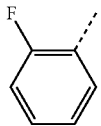

Table 13 provides 163 compounds of formula (IA) wherein A is 2-chlorophenyl (A13) and Y, $R_1$, $R_2$, $R_3$, $R_4$, $R_{9a}$, $R_{9b}$ and $R_{9c}$ are as defined in each row of Table Y.

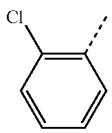

Table 14 provides 163 compounds of formula (IA) wherein A is 2-bromophenyl (A14) and Y, $R_1$, $R_2$, $R_3$, $R_4$, $R_{9a}$, $R_{9b}$ and $R_{9c}$ are as defined in each row of Table Y.

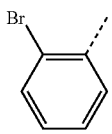

Table 15 provides 163 compounds of formula (IA) wherein A is 2-iodophenyl (A15) and Y, $R_1$, $R_2$, $R_3$, $R_4$, $R_{9a}$, $R_{9b}$ and $R_{9c}$ are as defined in each row of Table Y.

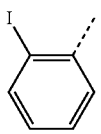

Table 16 provides 163 compounds of formula (IA) wherein A is 2,6-dichlorophenyl (A16) and Y, $R_1$, $R_2$, $R_3$, $R_4$, $R_{9a}$, $R_{9b}$ and $R_{9c}$ are as defined in each row of Table Y.

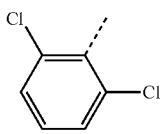

Table 17 provides 163 compounds of formula (IA) wherein A is 2-chloro-6-fluorophenyl (A17) and Y, $R_1$, $R_2$, $R_3$, $R_4$, $R_{9a}$, $R_{9b}$ and $R_{9c}$ are as defined in each row of Table Y.

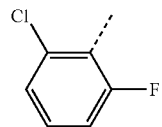

Table 18 provides 163 compounds of formula (IA) wherein A is 2,4,6-trifluorophenyl (A18) and Y, $R_1$, $R_2$, $R_3$, $R_4$, $R_{9a}$, $R_{9b}$ and $R_{9c}$ are as defined in each row of Table Y.

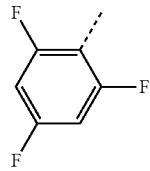

Table 19 provides 163 compounds of formula (IA) wherein A is 2-trifluoromethoxy-phenyl (A19) and Y, $R_1$, $R_2$, $R_3$, $R_4$, $R_{9a}$, $R_{9b}$ and $R_{9c}$ are as defined in each row of Table Y.

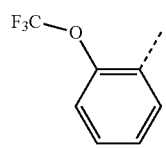

Table 20 provides 163 compounds of formula (IA) wherein A is 2-fluoro-6-methyl-phenyl (A20) and Y, $R_1$, $R_2$, $R_3$, $R_4$, $R_{9a}$, $R_{9b}$ and $R_{9c}$ are as defined in each row of Table Y.

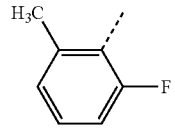

Table 21 provides 163 compounds of formula (IA) wherein A is 2-fluoro-6-methoxyphenyl (A21) and Y, $R_1$, $R_2$, $R_3$, $R_4$, $R_{9a}$, $R_{9b}$ and $R_{9c}$ are as defined in each row of Table Y.

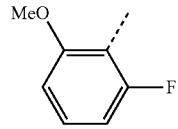

Table 22 provides 163 compounds of formula (IA) wherein A is 2-methyl-3-pyridyl (A22) and $R_1$, $R_2$, $R_3$, $R_4$, $R_{9a}$, $R_{9b}$ and $R_{9c}$ are as defined in each row of Table Y.

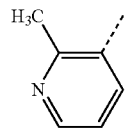

Table 23 provides 163 compounds of formula (IA) wherein A is 3-fluoro-2-pyridyl (A23) and Y, $R_1$, $R_2$, $R_3$, $R_4$, $R_{9a}$, $R_{9b}$ and $R_{9c}$ are as defined in each row of Table Y.

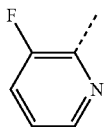

Table 24 provides 163 compounds of formula (IA) wherein A is 3-methyl-2-pyrazinyl (A24) and Y, $R_1$, $R_2$, $R_3$, $R_4$, $R_{9a}$, $R_{9b}$ and $R_{9c}$ are as defined in each row of Table Y.

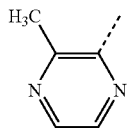

Table 25 provides 163 compounds of formula (IA) wherein A is 3-bromo-2-pyrazinyl (A25) and Y, $R_1$, $R_2$, $R_3$, $R_4$, $R_{9a}$, $R_{9b}$ and $R_{9c}$ are as defined in each row of Table Y.

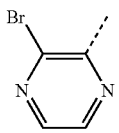

Table 26 provides 163 compounds of formula (IA) wherein A is 3-trifluoromethyl-2-pyrazinyl (A26) and Y, $R_1$, $R_2$, $R_3$, $R_4$, $R_{9a}$, $R_{9b}$ and $R_{9c}$ are as defined in each row of Table Y.

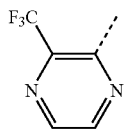

Table 27 provides 163 compounds of formula (IA) wherein A is 2-methyl-3-furyl (A27) and Y, $R_1$, $R_2$, $R_3$, $R_4$, $R_{9a}$, $R_{9b}$ and $R_{9c}$ are as defined in each row of Table Y.

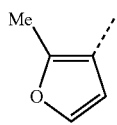

Table 28 provides 163 compounds of formula (IA) wherein A is 5-chloro-4-pyrimidinyl (A28) and Y, $R_1$, $R_2$, $R_3$, $R_4$, $R_{9a}$, $R_{9b}$ and $R_{9c}$ are as defined in each row of Table Y.

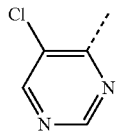

Table 29 provides 163 compounds of formula (IA) wherein A is 2-cyanophenyl (A29) and Y, $R_1$, $R_2$, $R_3$, $R_4$, $R_{9a}$, $R_{9b}$ and $R_{9c}$ are as defined in each row of Table Y.

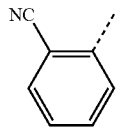

Table 30 provides 163 compounds of formula (IA) wherein A is 2-trifluoromethylthio-phenyl (A30) and Y, $R_1$, $R_2$, $R_3$, $R_4$, $R_{9a}$, $R_{9b}$ and $R_{9c}$ are as defined in each row of Table Y.

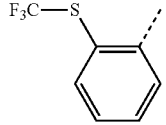

Table 31 provides 163 compounds of formula (IA) wherein A is 2-fluoro-3-pyridyl (A31) and Y, $R_1$, $R_2$, $R_3$, $R_4$, $R_{9a}$, $R_{9b}$ and $R_{9c}$ are as defined in each row of Table Y.

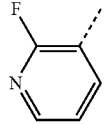

Table 32 provides 163 compounds of formula (IA) wherein A is 3-(difluoromethyl)-1-methyl-pyrazol-4-yl (A32) and $R_1$, $R_2$, $R_3$, $R_4$, $R_{9a}$, $R_{9b}$ and $R_{9c}$ are as defined in each row of Table Y.

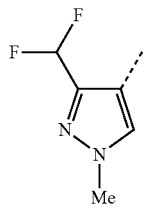

Table 33 provides 163 compounds of formula (IA) wherein A is 3-(trifluoromethyl)-1-methyl-pyrazol-4-yl (A33) and $R_1$, $R_2$, $R_3$, $R_4$, $R_{9a}$, $R_{9b}$ and $R_{9c}$ are as defined in each row of Table Y.

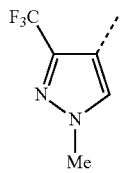

Examples of formula (II) made available are those where the substitutents B, Y, R1, R2, R3, R4 and R5 in formula (II) correspond to each row of Table Y above in context of formula (Ia). So for example, a compound of formula (II) in context of row Y.001 would be B is 4-chloro phenyl; Y is CH2; and R1 to R5 are each hydrogen.

Examples of formula (XIXa) made available are those where the substitutents B, Y, R1, R2, R3, and R4 in formula (XIXa) correspond to each row of Table Y above in context of formula (Ia). So for example, a compound of formula (XIXa) in context of row Y.001 would be B is 4-chloro phenyl; Y is CH2; and R1 to R4 are each hydrogen.

A compound of formula (I) has been found to control the damage caused by a pest and/or fungi.

In an embodiment, a compound of formula (I) can be used in agriculture.

Accordingly, the invention is moreover directed to a method of controlling damage and/or yield loss caused by a pest and/or fungi which comprises applying to a pest, to a locus of a pest, or to a plant susceptible to attack by a pest and/or fungi or to a plant propagation material an effective amount of a compound of formula (I).

The compounds according to the invention can be used for controlling, i.e. containing or destroying, pests and/or fungi which occur in particular on plants, especially on useful plants and ornamentals in agriculture, in horticulture and in forests, or on organs, such as fruits, flowers, foliage, stalks, tubers, seeds or roots, of such plants, and in some cases even plant organs which are formed at a later point in time remain protected against these pests.

The compounds of formula (I) according to the invention are preventively and/or curatively valuable active ingredients in the field of pest control, even at low rates of application, which can be used against pesticide resistant pests and fungi, which compounds of formula (I) have a very favorable biocidal spectrum and are well tolerated by warm-blooded species, fish and plants.

The compounds according to the invention may act against all or individual developmental stages of normally sensitive, but also resistant, animal pests, such as insects or representatives of the order *Acarina*. The insecticidal or acaricidal activity of the compounds according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

It has now been found that the compounds of formula I according to the invention have, for practical purposes, a very advantageous spectrum of activities for protecting animals and useful plants against attack and damage by nematodes. Accordingly, the present invention also makes available a nematicidal composition comprising compounds of the invention, such as formula (I).

The compounds of formula (I) are especially useful for the control of nematodes. Thus, in a further aspect, the invention also relates to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Eelonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus similis* and other *Radopholus* species; Reniform nematodes, *Rotylenchus robustus*, *Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

Particularly, the nematode species *Meloidogyne* spp., *Heterodera* spp., *Rotylenchus* spp. and *Pratylenchus* spp. can be controlled by compounds of the invention.

Examples of animal pests are:
from the order *Acarina*, for example,
*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order *Anoplura*, for example,
*Haematopinus* spp., *Linognathus* spp., *Pediculus* spp., *Pemphigus* spp. and *Phylloxera* spp.;

from the order *Coleoptera*, for example,
*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order *Diptera*, for example,
*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*,

*Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order *Hemiptera*, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

from the order *homoptera*, for example,

*Acyrthosium pisum*, *Adalges* spp, *Agalliana ensigera*, *Agonoscena targionii*, *Aleurodicus* spp., *Aleurocanthus* spp., *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* spp, *Nephotettix* spp., *Nilaparvata* spp., *Nippolachnus piri* Mats, *Odonaspis ruthae*, *Oregma lanigera Zehnter*, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order *Hymenoptera*, for example,

*Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order *Isoptera*, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order *Lepidoptera*, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order *Mallophaga*, for example,

*Damalinea* spp. and *Trichodectes* spp.;

from the order *Orthoptera*, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order *Psocoptera*, for example,

*Liposcelis* spp.;

from the order *Siphonaptera*, for example,

*Ceratophyllus* spp., *Ctenocephalides* spp. and *Xenopsylla cheopis*;

from the order *Thysanoptera*, for example,

*Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp;

from the order *Thysanura*, for example,

*Lepisma saccharina*.

In a further aspect, the invention may also relate to a method of controlling or preventing infestation of useful plants by phytopathogenic microorganisms, wherein a compound of formula (I) is applied as active ingredient to the plants, to parts thereof or the locus thereof. The compounds of formula (I) according to the invention are distinguished by activity, by being well tolerated by plants and by being environmentally safe. They have very useful curative, preventive and systemic properties and are used for protecting numerous useful plants. The compounds of formula (I) can be used to inhibit or destroy the diseases that occur on plants or parts of plants (fruit, blossoms, leaves, stems, tubers, roots) of different useful plants, while at the same time protecting also those parts of the plants that grow later e.g. from phytopathogenic microorganisms. It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Examples of fungi include: *Fungi imperfecti* (e.g. *Botrytis*, *Pyricularia*, *Helminthosporium*, *Fusarium*, *Septoria*, *Cercospora* and *Alternaria*); *Basidiomycetes* (e.g. *Rhizoctonia*, *Hemileia*, *Puccinia*); the *Ascomycetes* classes (e.g. *Venturia* and *Erysiphe*, *Podosphaera*, *Monilinia*, *Uncinula*); *Oomycetes* classes (e.g. *Phytophthora*, *Pythium*, *Plasmopara*); *Zygomycetes* (e.g., *Rhizopus* spp.); family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal plants and *Puccinia recondita*, also known as brown rust.

Among the plants and the possible diseases of these plants protected by the method according to the present invention, mention may be made of:

wheat, as regards controlling the following seed diseases: fusaria (*Microdochium nivale* and *Fusarium roseum*), stinking smut (*Tilletia caries, Tilletia controversa* or *Tilletia indica*), septoria disease (*Septoria nodorum*) and loose smut;

wheat, as regards controlling the following diseases of the aerial parts of the plant: cereal eyespot (*Tapesia yallundae, Tapesia acuiformis*), take-all (*Gaeumannomyces graminis*), foot blight (*F. culmorum, F. graminearum*), black speck (*Rhizoctonia cerealis*), powdery mildew (*Erysiphe graminis* form a specie tritici), rusts (*Puccinia striiformis* and *Puccinia recondita*) and septoria diseases (*Septoria tritici* and *Septoria nodorum*);

wheat and barley, as regards controlling bacterial and viral diseases, for example barley yellow mosaic; —barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis* form a specie hordei), dwarf leaf rust (*Puccinia hordei*) and leaf blotch (*Rhynchosporium secalis*);

potato, as regards controlling tuber diseases (in particular *Helminthosporium solani, Phoma tuberosa, Rhizoctonia solani, Fusarium solani*), mildew (*Plrytopthora infestans*) and certain viruses (virus Y);

potato, as regards controlling the following foliage diseases: early blight (*Alternaria solani*), mildew (*Phytophthora infestans*);

cotton, as regards controlling the following diseases of young plants grown from seeds: damping-off and collar rot (*Rhizoctonia solani, Fusarium oxysporum*) and black root rot (*Thielaviopsis basicola*);

protein yielding plants, for example peas, as regards controlling the following seed diseases: anthracnose (*Ascochyta pisi, Mycosphaerella* pinodes), fusaria (*Fusarium oxysporum*), grey mould (*Botrytis cinerea*) and mildew (*Peronospora pisi*);

oil-bearing plants, for example rape, as regards controlling the following seed diseases: *Phoma lingam, Alternaria brassicae* and *Sclerotinia sclerotiorum;* corn, as regards controlling seed diseases: (*Rhizopus* sp., *Penicillium* sp., [0104]*Trichoderma* sp., *Aspergillus* sp., and *Gibber ellafujikuroi*);

flax, as regards controlling the seed disease: *Alternaria linicola;* forest trees, as regards controlling damping-off (*Fusarium oxysporum, Rhizoctonia solani*);

rice, as regards controlling the following diseases of the aerial parts: blast disease (*Magnaporthe grisea*), bordered sheath spot (*Rhizoctonia solani*);

leguminous plants, as regards controlling the following diseases of seeds or of young plants grown from seeds: damping-off and collar rot (*Fusarium oxysporum, Fusarium roseum, Rhizoctonia solani, Pythium* sp.);

leguminous plants, as regards controlling the following diseases of the aerial parts: grey mould (*Botrytis* sp.), powdery mildews (in particular *Erysiphe cichoracearum, Sphaerotheca fuliginea* and *Leveillula taurica*), fusaria (*Fusarium oxysporum, Fusarium roseum*), leaf spot (*Cladosporium* sp.), alternaria leaf spot (*Alternaria* sp.), anthracnose (*Colletotrichum* sp.), septoria leaf spot (*Septoria* sp.), black speck (*Rhizoctonia solani*), mildews (for example *Bremia lactucae, Peronospora* sp., *Pseudoperonospora* sp., *Phytophthora* sp.);

fruit trees, as regards diseases of the aerial parts: monilia disease (*Monilia fructigenae, M. laxa*), scab (*Venturia inaequalis*), powdery mildew (*Podosphaera leucotricha*); —vine, as regards diseases of the foliage: in particular grey mould (*Botrytis cinerea*), powdery mildew (*Uncinula necator*), black rot (*Guignardia biwelli*) and mildew (*Plasmopara viticola*);

beetroot, as regards the following diseases of the aerial parts: cercospora blight (*Cercospora beticola*), powdery mildew (*Erysiphe beticola*), leaf spot (*Ramularia beticola*).

The fungicide composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

Compounds of this invention are effective for controlling nematode, insect, acarid pests and/or fungal pathogens of agronomic plants, both growing and harvested, when employed alone, they may also be used in combination with other biological active agents used in agriculture, such as one or more nematicides, insecticides, acaricides, fungicides, bactericides, plant activator, molluscicide, and pheromones (whether chemical or biological). Mixing the compounds of the invention or the compositions thereof in the use form as pesticides with other pesticides frequently results in a broader pesticidal spectrum of action. For example, the formula (I) compounds of this invention may be used effectively in conjunction or combination with pyrethroids, neonicotinoids, macrolides, diamides, phosphates, carbamates, cyclodienes, formamidines, phenol tin compounds, chlorinated hydrocarbons, benzoylphenyl ureas, pyrroles and the like.

The activity of the compositions according to the invention can be broadened considerably, and adapted to prevailing circumstances, by adding, for example, one or more insecticidally, acaricidally, nematicidally and/or fungicidally active agents. The combinations compounds of formula (I) with other insecticidally, acaricidally, nematicidally and/or fungicidally active agents may also have further surprising advantages which can also be described, in a wider sense, as synergistic activity. For example, better tolerance by plants, reduced phytotoxicity, pests or fungi can be controlled in their different development stages or better behaviour during their production, for example during grinding or mixing, during their storage or during their use.

The following list of pesticides together with which the compounds according to the invention can be used, is intended to illustrate the possible combinations by way of example.

The following combination of the compounds of formula (I) with another active compounds are preferred (the abbreviation "TX" means "one compound selected from the 163 compounds of each of Tables 1 to 33 of the present invention":

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfuram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, flupyradifurone+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, ometohate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfuram (alternative name) [CCN]+TX, sulfluramid (750)+TX, sulfotep (753)+TX, sulphur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Pasteuria penetrans*+TX, *Pasteuria thornei*+TX, *Pasteuria nishizawae*+TX, *Pasteuria ramosa*+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluoron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexylure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)-ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulphinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl)ether (IUPAC name) (909)+TX, bistrifluoron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+

TX, demeton-O (1038)+TX, demeton-O-methyl (224)+TX, demeton-S (1038)+TX, demeton-5-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, El 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos ($^{125}$I)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulphonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulphuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19]+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, yl-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-5-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)-ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-5-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid)

[120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulphur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid [2-(2,4-dichlorophenyl)-2-methoxy-1-methyl-ethyl]-amide (disclosed in WO 2008/148570)+TX, 1-[4-[4-[(5S)5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone+TX, 1-[4-[4-[5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone [1003318-67-9], both disclosed in WO 2010/123791, WO 2008/013925, WO 2008/013622 and WO 2011/051243 page 20)+TX, and 3-difluoromethyl-1-methyl-1H-pyrazole-4-carboxylic acid (3',4',5'-trifluoro-biphenyl-2-yl)-amide (disclosed in WO 2006/087343)+TX.

The references in square brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright© 1995-2004]; for example, the compound "acetoprole" is described under the internet address: http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The mass ratio of any two ingredients in each combination is selected as to give the desired, for example, synergistic action. In general, the mass ratio would vary depending on the specific ingredient and how many ingredients are present in the combination. Generally, the mass ratio between any two ingredients in any combination of the present invention, independently of one another, is from 100:1 to 1:100, including from 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34, 65:45, 64:46, 63:47, 62:48, 61:49, 60:40, 59:41, 58:42, 57:43, 56:44, 55:45, 54:46, 53:47, 52:48, 51:49, 50:50, 49:51, 48:52, 47:53, 46:54, 45:55, 44:56, 43:57, 42:58, 41:59, 40:60, 39:61, 38:62, 37:63, 36:64, 35:65, 34:66, 33:67, 32:68, 31:69, 30:70, 29:71, 28:72, 27:73, 26:74, 25:75, 24:76, 23:77, 22:78, 21:79, 20:80, 19:81, 18:82, 17:83, 16:84, 15:85, 14:86, 13:87, 12:88, 11:89, 10:90, 9:91, 8:92, 7:93, 6:94, 5:95, 4:96, 3:97, 2:98, to 1:99. Preferred mass ratios between any two components of present invention are from 75:1 to 1:75, more preferably, 50:1 to 1.50, especially 25:1 to 1:25, advantageously 10:1 to 1:10, such as 5:1 to 1:5, for example 1:3 to 3:1. The mixing ratios are understood to include, on the one hand, ratios by mass and also, on other hand, molar ratios.

Examples of application methods for the compounds of the invention and compositions thereof, that is the methods of controlling pests/fungi in the agriculture, are spraying, atomizing, dusting, brushing on, dressing, scattering or pouring—which are to be selected to suit the intended aims of the prevailing circumstances.

A preferred method of application in agriculture is application to the foliage of the plants (foliar application), it being possible to select frequency and rate of application to match the danger of infestation with the pest/fungi in question. Alternatively, the active ingredient can reach the plants via the root system (systemic action), by applying the compound to the locus of the plants, for example by application of a liquid composition of the compound into the soil (by drenching), or by applying a solid form of the compound in the form of granules to the soil (soil application). In the case of paddy rice plants, such granules can be metered into the flooded paddy-field.

Typical rates of application per hectare is generally 1 to 2000 g of active ingredient per hectare, in particular 10 to 1000 g/ha, preferably 10 to 600 g/ha, such as 50 to 300 g/ha.

The compounds of the invention and compositions thereof are also suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula I can be carried out by any known methods, such as spraying or by dusting the seeds before sowing or during the sowing/planting of the seeds.

Suitable target plants are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous plants, such as beans, lentils, peas or soya; oil plants, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals (such as flowers, amd lawn grass or turf).

In an embodiment, the plant is selected from cereals, corn, soybean, rice, sugarcane, vegetables and oil plants.

The term "plant" is to be understood as including also plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonizing nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (*Coleoptera*), two-winged insects (*Diptera*) and butterflies (*Lepidoptera*).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic plants are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G- protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain *Lepidoptera* insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain *Lepidoptera*, include the European corn borer.

Generally, a compound of the present invention is used in the form of a composition (e.g. formulation) containing a carrier. A compound of the invention and compositions thereof can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

A formulation typically comprises a liquid or solid carrier and optionally one or more customary formulation auxiliaries, which may be solid or liquid auxiliaries, for example unepoxidized or epoxidized vegetable oils (for example epoxidized coconut oil, rapeseed oil or soya oil), antifoams, for example silicone oil, preservatives, clays, inorganic compounds, viscosity regulators, surfactant, binders and/or tackifiers. The composition may also further comprise a fertilizer, a micronutrient donor or other preparations which influence the growth of plants as well as comprising a combination containing the compound of the invention with one or more other biologically active agents, such as bactericides, fungicides, nematocides, plant activators, acaricides, and insecticides.

Accordingly, the present invention also makes available a composition comprising a compound of the invention and an agronomicaly carrier and optionally one or more customary formulation auxiliaries.

The compositions are prepared in a manner known per se, in the absence of auxiliaries for example by grinding, screening and/or compressing a solid compound of the present invention and in the presence of at least one auxiliary for example by intimately mixing and/or grinding the compound of the present invention with the auxiliary (auxiliaries). In the case of solid compounds of the invention, the grinding/milling of the compounds is to ensure specific particle size. These processes for the preparation of the compositions and the use of the compounds of the invention for the preparation of these compositions are also a subject of the invention.

Examples of compositions for use in agriculture are emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—a compound according to the invention and the type of composition is to be selected to suit the intended aims and the prevailing circumstances.

Examples of suitable liquid carriers are unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Examples of solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulphuric ester or of a fatty alcohol sulfate mixture prepared from natural fatty acids. This group also includes the salts of the sulphuric esters and sulfonic acids of fatty alcohol/ethylene oxide adducts. The sulfonated benzimidazole derivatives preferably contain 2 sulphonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of compound according to the present invention and 1 to 99.9%, especially 5 to 99.9%, of at least one solid or liquid carrier, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable Concentrates:
  active ingredient: 1 to 95%, preferably 5 to 20%
  surfactant: 1 to 30%, preferably 10 to 20%
  solvent: 5 to 98%, preferably 70 to 85%
Dusts:
  active ingredient: 0.1 to 10%, preferably 0.1 to 1%
  solid carrier: 99.9 to 90%, preferably 99.9 to 99%
Suspension Concentrates and Flowable Concentrates:
  active ingredient: 5 to 75%, preferably 10 to 50%
  water: 94 to 24%, preferably 88 to 30%
  surfactant: 1 to 40%, preferably 2 to 30%
Wettable Powders:
  active ingredient: 0.5 to 90%, preferably 1 to 80%
  surfactant: 0.5 to 20%, preferably 1 to 15%
  solid carrier: 5 to 99%, preferably 15 to 98%
Granulates:
  active ingredient: 0.5 to 30%, preferably 3 to 15%
  solid carrier: 99.5 to 70%, preferably 97 to 85%

FORMULATION EXAMPLES

%=Percent by Weight

Example F1

| Emulsion concentrates | a) | b) | c) |
| --- | --- | --- | --- |
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2

| Solutions | a) | b) | c) | d) |
| --- | --- | --- | --- | --- |
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3

| Granules | a) | b) | c) | d) |
| --- | --- | --- | --- | --- |
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4

| Dusts | a) | b) |
| --- | --- | --- |
| Active ingredient | 2% | 5% |
| Highly disperse silica | 1% | 5% |

| Dusts | a) | b) |
|---|---|---|
| Talc | 97% | — |
| Kaolin | — | 90% |

Ready-to-use dusts are obtained by intimately mixing the carriers and the active ingredient.

Example F5

| Wettable powders | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutyl-naphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6

| Extruder granules | |
|---|---|
| Active ingredient | 10% |
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7

| Coated granules | |
|---|---|
| Active ingredient | 3% |
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8

| Suspension concentrate | |
|---|---|
| Active ingredient | 40% |
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

Example F9

| Powders for dry seed treatment | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

Example F10

| Emulsifiable concentrate | |
|---|---|
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

Example F11

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Examples of foliar formulation types for pre-mix compositions are:
  GR: Granules
  WP: wettable powders
  WG: water dispersable granules (powders)
  SG: water soluble granules
  SL: soluble concentrates
  EC: emulsifiable concentrate
  EW: emulsions, oil in water
  ME: micro-emulsion
  SC: aqueous suspension concentrate
  CS: aqueous capsule suspension
  OD: oil-based suspension concentrate, and
  SE: aqueous suspo-emulsion.

Whereas, examples of seed treatment formulation types for pre-mix compositions are:
  WS: wettable powders for seed treatment slurry
  LS: solution for seed treatment
  ES: emulsions for seed treatment
  FS: suspension concentrate for seed treatment
  WG: water dispersible granules, and
  CS: aqueous capsule suspension.

Examples of formulation types suitable for tank-mix compositions are solutions, dilute emulsions, suspensions, or a mixture thereof, and dusts.

As with the nature of the formulations, the methods of application, such as foliar, drench, spraying, atomizing, dusting, scattering, coating or pouring, are chosen in accordance with the intended objectives and the prevailing circumstances.

The tank-mix compositions are generally prepared by diluting with a solvent (for example, water) the one or more pre-mix compositions containing different pesticides, and optionally further auxiliaries.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

Generally, a tank-mix formulation for foliar or soil application comprises 0.1 to 20%, especially 0.1 to 15%, of the desired ingredients, and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50, %, by mass of the desired ingredients, and 99.5 to 0.1, especially 99 to 5, %, by mass of a solid or liquid adjuvant (including, for example, a solvent such as water), where the auxiliaries (or adjuvant) can be a surfactant in an amount of 0 to 50, especially 0.5 to 40, %, by mass based on the mass of the pre-mix formulation.

A compound of the formula (I) is in a preferred embodiment, independent of any other embodiments, is in the form of a plant propagation material treating (or protecting) composition, wherein said plant propagation material protecting composition comprises additionally a colouring agent. The plant propagation material protecting composition or mixture may also comprise at least one polymer from water-soluble and water-dispersible film-forming polymers that improve the adherence of the active ingredients to the treated plant propagation material, which polymer generally has an average molecular weight of at least 10,000 to about 100,000.

The combinations of the present invention (i.e. those comprising a compound of the present invention and one or more other biological active agents) may be applied simultaneously or sequentially.

In the event, the ingredients of a combination are applied sequentially (i.e., one after the other), the ingredients are applied sequentially within a reasonable period of each other to attain the biological performance, such as within a few hours or days. The order of applying the ingredients in the combination, i.e., whether the compounds of formula (I) should be applied first or not is not essential for working the present invention.

In the event ingredients of the combinations are applied simultaneously in the present invention, they may be applied as a composition containing the combination, in which case (A) the compound of formula (I) and the one or more other ingredients in the combinations can be obtained from separate formulation sources and mixed together (known as a tank-mix, ready-to-apply, spray broth, or slurry), or (B) the compound of formula (I) and the one or more other ingredients can be obtained as single formulation mixture source (known as a pre-mix, ready-mix, concentrate, or formulated product).

In an embodiment, independent of other embodiments, a compound according to the present invention is applied as a combination. Accordingly, the present invention also provides a composition comprising a compound according the invention as herein described and one or more other biological active agents, and optionally one or more customary formulation auxiliaries; which may be in the form of a tank-mix or pre-mix composition.

Alternative to the actual synergistic action with respect to biological activity, the combinations according to the invention also can have surprising advantageous properties which can also be described, in a wider sense, as synergistic activity. Examples of such advantageous properties that may be mentioned are: advantageous behaviour during formulation and/or upon application, for example upon grinding, sieving, emulsifying, dissolving or dispensing; increased storage stability; improved stability to light; more advantageous degradability; improved toxicological and/or ecotoxicological behaviour; or any other advantages familiar to a person skilled in the art.

The compounds of the present invention for use in agriculture is preferably as a nematicide.

The compounds of the present invention may also find application in other fields, such as one or more of protection of stored goods and store rooms, the protection of raw materials (such as wood and textiles), floor coverings and buildings, and in hygiene management—especially the protection of humans, domestic animals and productive livestock against pests. The invention therefore also makes available pesticidal compositions for such uses and the methods therefor. The composition would need to be modified for use in a particular use, and a skilled person would be able to make available such compositions for any particular use.

In the hygiene sector, the compositions according to the invention are active against ectoparasites such as hard ticks, soft ticks, mange mites, harvest mites, flies (biting and licking), parasitic fly larvae, lice, hair lice, bird lice and fleas. Examples of such parasites are:

Of the order *Anoplurida: Haematopinus* spp., *Linognathus* spp., *Pediculus* spp. and *Phtirus* spp., *Solenopotes* spp.

Of the order *Mallophagida: Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order *Diptera* and the suborders *Nematocerina* and *Brachycerina*, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order *Siphonapterida*, for example *Pulex* spp., *Ctenocephalides* spp., *Xenopsylla* spp., *Ceratophyllus* spp.

Of the order *Heteropterida*, for example *Cimex* spp., *Triatoma* spp., *Rhodnius* spp., *Panstrongylus* spp.

Of the order *Blattarida*, for example *Blatta orientalis, Periplaneta americana, Blattelagermanica* and *Supella* spp.

Of the subclass *Acaria (Acarida)* and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders *Actinedida (Prostigmata)* and *Acaridida (Astigmata)*, for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings. The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The application methods for applying a compound or a composition thereof to stored goods, store rooms, raw materials (such as wood and textiles), floor coverings and buildings, and in hygiene management is known in the art.

The invention also provides a method for treating, curing, controlling, preventing and protecting warm-blooded animals, including humans, and fish against infestation and infection by helminths, arachnids and arthropod endo- and ectoparasites which comprises orally, topically or parenterally administering or applying to said animals an anthelmintically, acaricidally or endo- or ectoparasiticidally effective amount of compound of formula (I).

The above method is particularly useful for controlling and preventing helminth, nemtode, acarid and arthropod endo- and ectoparasitic infestations and infections in warm-blooded animals such as cattle, sheep, swine, camels, deer, horses, poultry, fish, rabbits, goats, mink, fox, chinchillas, dogs and cats as well as humans.

In the context of control and prevention of infestation and infections in warm-blooded animals, compounds of invention are especially useful for the control of helminths and nematodes. Examples for helminths are members of the class Trematoda, commonly known as flukes or flatworms, especially members of the genera *Fasciola, Fascioloides, Paramphistomu, Dicrocoelium, Eurytrema, Ophisthorchis, Fasciolopsis, Echinostoma* and *Paragonimus*. Nematodes which can be controlled by the formula (I) compounds include the genera *Haemonchus, Ostertagia, Cooperia, Oesphagastomu, Nematodirus, Dictyocaulus, Trichuris, Dirofilaria, Ancyclostoma, Ascaria* and the like.

The compound of this invention may also control endoparasitic arthropod infestations such as cattle grub and stomach bot. In addition, acarid and arthropod ectoparasitic infestations in warm-blooded animals and fish including biting lice, sucking lice, bot flies, biting flies, muscoid flies, flies, myiasitic fly larvae, gnats, mosquitoes, fleas, mites, ticks, nasal bots, keds and chiggers may be controlled, prevented or eliminated by the compounds of this invention. Biting lice include members of *Mallophaga* such as *Bovicola bovis, Trichodectes canis* and *Damilina ovis*. Sucking lice include members of *Anoplura* such as *Haematopinus eurysternus, Haematopinus suis, Linognathus vituli* and *Solenopotes capillatus*. Biting flies include members of *Haematobia*. Ticks include *Boophilus, Rhipicephalus, Ixodes, Hyalomma, Amblyomma* and *Dermacentor*. The compounds of the invention may also be used to control mites which are parasitic on warm-blooded mammals and poultry including mites of the orders *Acariformes* and *Parasitiformes*.

For oral administration to warm-blooded animals, the compounds of the invention may be formulated as animal feeds, animal feed premixes, animal feed concentrates, pills, solutions, pastes, suspensions, drenches, gels, tablets, boluses and capsules. In addition, the compounds of the invention may be administered to the animals in their drinking water. For oral administration, the dosage form chosen should provide the animal with about 0.01 mg/kg to 100 g/kg of animal body weight per day of the compound of the invention.

Alternatively, the compounds of the invention may be administered to animals parenterally, for example, by intraruminal, intramuscular, intravenous or subcutaneous injection. The compounds of the invention may be dispersed or dissolved in a physiologically acceptable carrier for subcutaneous injection. Alternatively, the compounds of the invention may be formulated into an implant for subcutaneous administration. In addition the compounds of the invention may be transdermally administered to animals. For parenteral administration, the dosage form chosen should provide the animal with about 0.01 mg/kg to 100 mg/kg of animal body weight per day of the compound of the invention.

The compounds of the invention may also be applied topically to the animals in the form of dips, dusts, powders, collars, medallions, sprays and pour-on formulations. For topical application, dips and sprays usually contain about 0.5 ppm to 5,000 ppm and preferably about 1 ppm to 3,000 ppm of the compound of the invention. In addition, the compounds of the invention may be formulated as ear tags for animals, particularly quadrupeds such as cattle and sheep.

The compounds of the invention may also be used in combination or conjunction with one or more other parasiticidal compounds (to broaden the spectrum of activity) including, but not limited to, anthelmintics, such as benzimidazoles, piperazine, levamisole, pyrantel, praziquantel and the like; endectocides such as avermectins, milbemycins and the like; ectoparasiticides such as arylpyrroles, organophosphates, carbamates, gamabutyric acid inhibitors including fipronil, pyrethroids, spinosads, imidacloprid and the like; insect growth regulators such as pyriproxyfen, cyromazine and the like; and chitin synthase inhibitors such as benzoylureas including flufenoxuron.

The parasiticidal compositions of the present invention include a parasiticidally effective amount of a compound of the invention or combinations thereof admixed with one or more physiologically tolerable inert, solid or liquid carriers known from veterinary medicinal practice for oral, percutaneous and topical administration. Such compositions may comprise further additives, such as stabilizers, anifoams, viscosity regulators, binders and tackifiers, whereas commercial products will preferably be formulated as concentrates, the end user will normally employ dilute formulations.

The compositions according to the present invention may also be used for the preparation of composition useful to curatively or preventively treat human and animal fungal diseases such as, for example, mycoses, dermatoses, *trichophyton* diseases and candidiases or diseases caused by *Aspergillus* spp., for example *Aspergillus fumigatus*.

In an embodiment, independent of any other embodiments, a compound of formula (I) is a anti-helminth compound.

In an embodiment, independent of any other embodiments, a compound of formula (I) is a pesticidal compound, preferably a nematicidal compound.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The disclosure in the present application makes available each and every combination of embodiments disclosed herein.

The following Examples serve to illustrate the invention. They do not limit the invention. Temperatures are given in degrees Celsius; mixing ratios of solvents are given in parts by volume.

EXAMPLES

Preparation Examples

Example P1

Preparation of N-[cis-2-(4-chlorophenyl)oxetan-3-yl]-2-(trifluoromethyl)benzamide (compound 57.010)

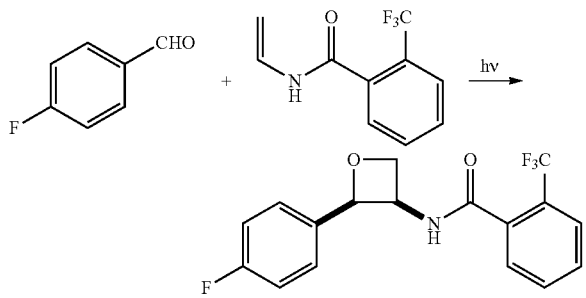

A solution of 4-fluorobenzaldehyde (288 mg, 2.32 mmol) and 2-trifluoromethyl-N-vinyl-benzamide (example P8b) (1 g, 4.65 mmol) in acetonitrile (15 ml) was irradiated with a sodium vapour lamp through a quarz filter for 7 days. The cloudy reaction mixture was evaporated down and the crude half-solid (1.6 g) was chromatographed on silica with EtOAc/cyclohexane, then again with MeOH/dichloromethane and again with EtOAc/cyclohexane to yield 43 mg (3%) of N-[cis-2-(4-chlorophenyl)oxetan-3-yl]-2-(trifluoromethyl)benzamide.

1H-NMR (CDCl3) 4.51 (1H, t); 5.17 (1H, t); 5.48 (1H, M); 5.71 (1H, br d); 6.08 (1H, d); 6.93 (1H, d); 7.12 (2H, t); 7.38 (2H, m); 7.47 (2H, m); 7.63 (1H, d).

Example P2

Preparation of cis N-[2-(4-chlorophenyl)cyclobutyl]-2-(trifluoromethyl)benzamide (compound 57.006)

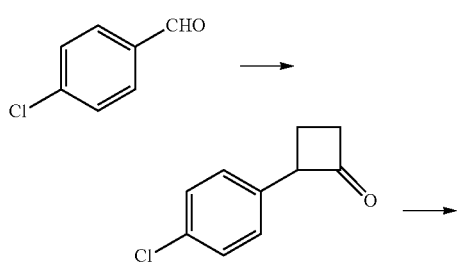

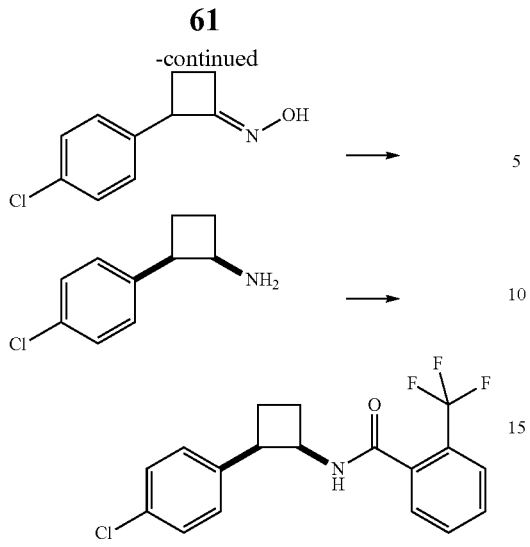

a. Preparation of 2-(4-chlorophenyl)cyclobutanone

To a stirred solution of 4-chloro-benzaldehyde (142 mg, 1 mmol) and cyclopropyldiphenylsulfonium tetrafluoroborate (317 mg, 1 mmol) in 10 ml dry THF, cooled to 0° C., was added dropwise, with stirring, a slurry of potassium tert. butoxide (1.4 ml 1M). After addition was complete the reaction was stirred 30 min. and 1M tetrafluoroboric acid (10% in THF) (10 ml) was added. The mixture was allowed to warm to room temperature and was taken up into ether and the ether solution was washed with saturated $NaHCO_3$, brine and water and was dried. Filtration and concentration by rotary evaporation gave an oil. Chromatography over silica gel and elution i-Hx:ether 5:1 gave 2-(4-chlorophenyl)cyclobutanone as an oil. (180 mg, 83%).

1H-NMR ($CDCl_3$) 2.20 (1H, m); 2.57 (1H, m); 3.06 (1H, m); 3.23 (1H, m); 4.51 (1H, m); 7.20 (2H, m); 7.29 (3H, m);

b. Preparation of 2-(4-chlorophenyl)cyclobutanone oxime

A solution of 2-(4-chlorophenyl)cyclobutanone (1.122 g, 6.09 mmol), hydroxylamine hydrochloride (3.541 g. 8.2 eq.) and 36 ml of 5% NaOH in 30 ml EtOH was heated at reflux for 2 h. The solution was cooled, adjusted to pH 6, and extracted with $CHCl_3$. The organic extract was washed with brine and dried. Filtration and concentration yielded 2-(4-chlorophenyl)cyclobutanone oxime as an oil. 1 g (84%)

1H-NMR ($CDCl_3$) 2.13 (1H, m); 2.53 (1H, m); 3.01 (2H, m); 4.40 (1H, m); 7.27 (5H, m);

c. Preparation of 2-(4-chlorophenyl)cyclobutanamine

To a solution of 2-(4-chlorophenyl)cyclobutanone oxime (200 mg, 1 mmol) in methanol (5 ml) was added $MoO_3$ (205 mg, 1.4 eq.) and sodium borohydride (394 mg, 10 eq) at 0° C. After stirring at rt for 2 h the solvent was evaporated. A mixture of $H_2O$ and $CH_2Cl_2$ was added. Organic phase was separated, washed with brine, dried and concentrated in vacuo. 120 mg of product-amine was isolated as a mixture of cis and trans isomers 2:1. The crude product without purification was used for the next reaction.

d. Preparation of N-[2-(4-chlorophenyl)cyclobutyl]-2-(trifluoromethyl)benzamide

To a solution of 2-(4-chlorophenyl)cyclobutanamine (105 mg, 0.55 mmol) and triethylamine (140 mg 2.5 eq.) in THF was added 2-trifluoromethyl-benzoylchloride (127.46 mg, 1.1 eq.) at 0° C. The RM was stirred at rt for 2 h. $Et_3N.HCl$ was filtered off and the THF was evaporated. The residue—mixture of two isomers cis and trans (2:1) was purified and separated with chromatography on silica gel, eluent i-Hx:diethylether 1:1, ($KMnO_4$ stain). N-[cis-2-(4-chlorophenyl)cyclobutyl]-2-(trifluoromethyl)benzamide (cis) (33 mg, m.p. 147-9° C.) and its trans isomer (17 mg, m.p. 117-9° C.) were isolated as crystalline products.

Example P3

Preparation of 2-(4-chlorophenyl)cyclobutanone (alternative)

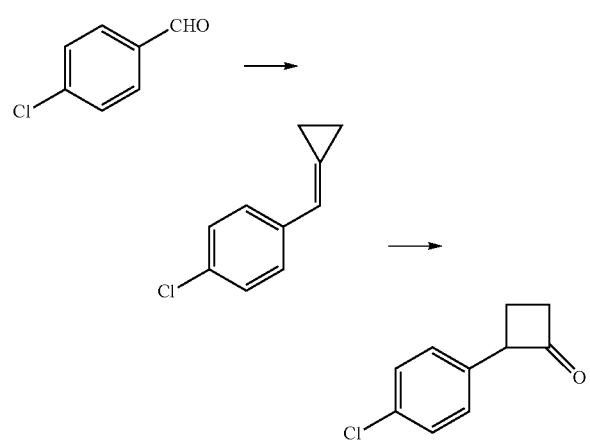

a. Preparation of 1-chloro-4-(cyclopropylidenemethyl)benzene

To a suspension of (4-bromopropyl)triphenylphosphonium bromide (29.3 g) in anhydrous THF (200 ml) was added in 5 separate portions 15 mins apart potassium tert. butoxide (14.19 g, 2.2 eq.) to give a yellow suspension. The mixture was heated to reflux for 10 min and 4-dichlorobenzaldehyde (8.08 g, 56.9 mmol) was added to give an orange suspension. The reaction mixture was stirred and then heated at reflux for 4 h. The RM was then cooled to room temperature, and filtered through a Celite pad. The solvent was removed in vacuo, and the resulting crude material (9 g) was subjected to flash chromatography with i-hexane as an eluent, affording 1-chloro-4-(cyclopropylidenemethyl)benzene (5 g, 53%).

1H-NMR ($CDCl_3$) 1.19 (2H, m); 1.41 (2H, m); 6.70 (1H, m); 7.27 (2H, m); 7.46 (2H, m)

b. Preparation of 2-(4-chlorophenyl)cyclobutanone

To a solution of 1-chloro-4-(cyclopropylidenemethyl)benzene (5 g, 30 mmol) in $CH_2Cl_2$ (80 ml) was added in 5 separate portions m-chloroperbenzoic acid (5.3 g, 30 mmol) at 0° C. After stirring at 0° C. for 3 h, the reaction mixture was washed with saturated $NaHCO_3$ aqueous solution and brine, dried over $Na_2SO_4$ and concentrated. To the crude product in $CH_2Cl_2$ (40 ml) was added 10% $HBF_4$ (11.6 ml 48% $HBF_4$ and 46 ml $H_2O$). After stirring for 17 h, the mixture was extracted with $CH_2Cl_2$, washed with saturated $NaHCO_3$ aq. solution and brine. The solvent was removed in vacuo, and the residue was purified by column chromatography on silica gel (eluent i-hexane, KMnO₄ stain) to give 2-(4-chlorophenyl)cyclobutanone (3.470 g, 64%).

Table 57 shows selected melting point, selected HPLC-MS, and selected NMR data for compounds of the present invention. CDCl₃ was used as the solvent for NMR measurements, unless otherwise stated. No attempt is made to list all characterising data in all cases.

In Table 57 and throughout the description that follows, temperatures are given in degrees Celsius; "NMR" means nuclear magnetic resonance spectrum; HPLC is high pressure liquid chromatography; MS stands for mass spectrum; "%" is percent by weight, unless corresponding concentrations are indicated in other units. The following abbreviations are used throughout this description:

| | |
|---|---|
| m.p. = melting point [° C.] | b.p. = boiling point. |
| S = singlet | br = broad |
| d = doublet | dd = doublet of doublets |
| t = triplet | q = quartet |
| m = multiplet | ppm = parts per million |

Table 57 below is a list of characterised compounds of the formula Id. This represents formula I, wherein Y is either O or CH₂ and R1, R2, R3, R4, and R5 are H.

TABLE 57

Characterising data (Id)

| Cpd no. | Y | R9a, R9b, R9c* | A | m.p. [° C.] | Retention time [min.] | M + H⁺ |
|---|---|---|---|---|---|---|
| 57.001 | CH₂ | 4-OCF3 | A1 | 110-112 | | |
| 57.002 | CH₂ | 4-OCF3 | A9 | 120-123 | | |
| 57.003 | CH₂ | 4-OCF3 | A6 | 128-131 | | |
| 57.004 | O | 4-Cl | A6 | | | NMR |
| 57.005 | CH₂ | 4-Cl | A1 | 138-140 | | |
| 57.006 | CH₂ | 4-Cl | A6 | 147-149 | | |
| 57.007 | CH₂ | 4-Cl | A5 | 149-150 | | |
| 57.008 | CH₂ | 2,4-Cl2 | A1 | 124-126 | | |
| 57.009 | CH₂ | 2,4-Cl2 | A6 | 126-128 | | |
| 57.010 | O | 4-F | A6 | | 1.7 | 340 |
| 57.011 | CH₂ | 2,4-Cl2 | A5 | 157-159 | | NMR |
| 57.012 | CH₂ | 2,4-Cl2 | A10 | | | NMR |
| 57.013 | CH₂ | 4-Cl | A10 | | | NMR |
| 57.014 | CH₂ | 2-F, 4-Cl | A1 | 126-129 | | |
| 57.015 | CH₂ | 2-F, 4-Cl | A6 | | | NMR |
| 57.016 | CH₂ | 4-OCHF2 | A1 | | 1.71 | 354 |
| 57.017 | CH₂ | 4-OCHF2 | A6 | | 1.78 | 386 |
| 57.018 | CH₂ | 4-Cl | A7 | 98-101 | | |
| 57.019 | CH₂ | 4-Cl | A31 | 86-89 | | |
| 57.020 | CH₂ | 4-Cl | A3 | 115-116 | | |
| 57.021 | CH₂ | 4-Cl | A23 | 80-82 | | |
| 57.022 | CH₂ | 4-Cl | A2 | 138-141 | | |
| 57.023 | CH₂ | 4-Cl | A26 | 156-158 | | |
| 57.024 | CH₂ | 4-Cl | A7 | 122-124 | | |
| 57.025 | CH₂ | 2,4-Cl2 | A3 | 109-111 | | |
| 57.026 | CH₂ | 2,4-Cl2 | A31 | 96-102 | | |
| 57.027 | CH₂ | 2,4-Cl2 | A7 | 124-128 | | |
| 57.028 | CH₂ | 2,4-Cl2 | A23 | 119-121 | | |
| 57.029 | CH₂ | 2,4-Cl2 | A2 | 92-94 | | |
| 57.030 | CH₂ | 2,4-Cl2 | A26 | 141-143 | | |
| 57.031 | CH₂ | 2,4-Cl2 | A4 | 82-84 | | |
| 57.032 | CH₂ | 4-F | A1 | 134-135 | | |
| 57.033 | CH₂ | 4-F | A6 | 143-144 | | |
| 57.034 | CH₂ | 4-Br | A1 | 137-138 | | |
| 57.035 | CH₂ | 4-Br | A6 | 144-145 | | |
| 57.036 | not tested | 4-F | A5 | 156-157 | | |
| 57.037 | CH₂ | 4-Br | A5 | 139-140 | | |
| 57.038 | CH₂ | 4-cPr | A5 | 157-158 | | |
| 57.039 | CH₂ | 4-CN | A5 | 170-174 | | |
| 57.04 | CH₂ | 4-F | A3 | 111-114 | | |
| 57.041 | CH₂ | 4-F | A4 | 95-98 | | |
| 57.042 | CH₂ | 4-F | A23 | 75-80 | | |
| 57.043 | CH₂ | 4-F | A2 | 131-132 | | |
| 57.044 | CH₂ | 4-F | A26 | 122-124 | | |
| 57.045 | CH₂ | 4-Br | A2 | 167-169 | | |
| 57.046 | CH₂ | 4-Br | A26 | 166-170 | | |
| 57.047 | O | 2,4,6-F3 | A6 | | 0.89 | 376 |
| 57.048 | O | 4-OCHF2 | A6 | 115-120 | | |
| 57.049 | O | 4-CF3 | A6 | 123-125 | | |
| 57.050 | O | 2-F, 4-CF3 | A6 | 99-108 | | |
| 57.051 | O | 2,4-F2 | A1 | 125-130 | | |
| 57.052 | O | 2,4,6-F3 | A1 | 130-136 | | |
| 57.053 | O | 4-F | A1 | 95-101 | | |
| 57.054 | O | 4-F | A5 | 107-127 | | |
| 57.055 | O | 2,4-F2 | A6 | 129-132 | | |
| 57.056 | O | 2,4-F2 | A5 | 131-134 | | |
| 57.057 | O | 2,4,6-F3 | A5 | 143-146 | | |
| 57.058 | CH2 | 2,4-F2 | A6 | 106-108 | | |
| 57.059 | CH2 | 2,4-F2 | A3 | 124-126 | | |
| 57.060 | CH2 | 2,4-F2 | A5 | 146-147 | | |
| 57.061 | CH2 | 2,4-F2 | A26 | 108-110 | | |
| 57.062 | CH2 | 2-Cl, 4-CF3 | A6 | 131-133 | | |
| 57.063 | CH2 | 2-Cl, 4-CF3 | A3 | 95-97 | | |
| 57.064 | CH2 | 2-Cl, 4-CF3 | A5 | 137-139 | | |
| 57.065 | CH2 | 2-Cl, 4-CF3 | A26 | 112-114 | | |
| 57.066 | CH2 | 2-F, 4-CF3 | A6 | 110-112 | | |
| 57.067 | CH2 | 2-F, 4-CF3 | A3 | 109-111 | | |
| 57.068 | CH2 | 2-F, 4-CF3 | A5 | 151-153 | | |
| 57.069 | CH2 | 2-F, 4-CF3 | A26 | 152-154 | | |
| 57.070 | CH2 | 2,4-Cl2 | A10 | | 1.41 | 322.27 |
| 57.071 | CH2 | 2,4-Cl2 | A13 | | 1.75 | 354.04 |
| 57.072 | CH2 | 2,4-Cl2 | A9 | | 1.74 | 334.21 |
| 57.073 | CH2 | 2,4-Cl2 | A18 | | 1.73 | 374.17 |
| 57.074 | CH2 | 2,4-Cl2 | A27 | | 1.66 | 324.17 |
| 57.075 | CH2 | 2,4-Cl2 | A4 | | 1.66 | 355.14 |
| 57.076 | CH2 | 2,4-Cl2 | A12 | | 1.76 | 338.47 |
| 57.077 | CH2 | 2,4-Cl2 | A17 | | 1.74 | 372.14 |
| 57.078 | CH2 | 2,4-Cl2 | A11 | | 1.8 | 335.19 |
| 57.079 | CH2 | 2,4-Cl2 | A29 | | 1.63 | 345.2 |
| 57.080 | CH2 | 2,4-Cl2 | A21 | | 1.72 | 368.2 |
| 57.081 | CH2 | 2,4-Cl2 | A20 | | 1.74 | 352.24 |
| 57.082 | CH2 | 2,4-Cl2 | A24 | | 1.63 | 336.17 |
| 57.083 | CH2 | 2,4-Cl2 | A16 | | 1.8 | 388.09 |
| 57.084 | CH2 | 2,4-Cl2 | A12 | | 1.8 | 446.14 |
| 57.085 | CH2 | 2,4-Cl2 | A19 | | 1.89 | 404.18 |
| 57.086 | CH2 | 2,4-Cl2 | A8 | | 1.8 | 406.18 |
| 57.087 | CH2 | 2,4-Cl2 | A14 | | 1.76 | 397.97 |
| 57.088 | CH2 | 2,4-Cl2 | A22 | | 1.17 | 335.22 |
| 57.089 | CH2 | 2,4-Cl2 | A30 | | 1.92 | 420.19 |
| 57.090 | CH2 | 2,4-Cl2 | A28 | | 1.59 | 356.14 |
| 57.091 | CH2 | 4-Cl | A10 | | 1.29 | 288.32 |
| 57.092 | CH2 | 4-Cl | A13 | | 1.62 | 320.28 |
| 57.093 | CH2 | 4-Cl | A9 | | 1.63 | 300.16 |
| 57.094 | CH2 | 4-Cl | A18 | | 1.62 | 340.09 |
| 57.095 | CH2 | 4-Cl | A27 | | 1.55 | 290.23 |
| 57.096 | CH2 | 4-Cl | A4 | | 1.54 | 321.13 |
| 57.097 | CH2 | 4-Cl | A12 | | 1.64 | 304.22 |

TABLE 57-continued

Characterising data (Id)

| Cpd no. | Y | R9a, R9b, R9c* | A | m.p. [° C.] | Retention time [min.] | M + H+ |
|---|---|---|---|---|---|---|
| 57.098 | CH2 | 4-Cl | A17 | | 1.63 | 338.45 |
| 57.099 | CH2 | 4-Cl | A11 | | 1.65 | 301.17 |
| 57.100 | CH2 | 4-Cl | A29 | | 1.45 | 310.98 |
| 57.101 | CH2 | 4-Cl | A21 | | 1.56 | 334.22 |
| 57.102 | CH2 | 4-Cl | A20 | | 1.63 | 318.18 |
| 57.103 | CH2 | 4-Cl | A24 | | 1.49 | 301.73 |
| 57.104 | CH2 | 4-Cl | A16 | | 1.69 | 354.18 |
| 57.105 | CH2 | 4-Cl | A12 | | 1.69 | 411.53 |
| 57.106 | CH2 | 4-Cl | A19 | | 1.78 | 370.22 |
| 57.107 | CH2 | 4-Cl | A8 | | 1.71 | 372.19 |
| 57.108 | CH2 | 4-Cl | A14 | | 1.64 | 364.26 |
| 57.109 | CH2 | 4-Cl | A22 | | 1.02 | 301.29 |
| 57.110 | CH2 | 4-Cl | A30 | | 1.83 | 386.28 |
| 57.111 | CH2 | 4-Cl | A28 | | 1.45 | 322.05 |

*any one of $R_{9a}$, $R_{9b}$ and $R_{9c}$ is hydrogen depending on the substituents defined in each row +NMR data:

57.011:
2.08 (1H, m); 2.37 (2H, m); 2.62 (1H, m); 4.26 (1H, m); 5.05 (1H, m); 5.42 (1H, m); 7.32 (2H, m); 7.41 (1H, s); 7.49 (1H, m); 7.65 (1H, m); 8.69 (1H, d).

57.012:
2.13 (1H, m); 2.39 (2H, m); 2.62 (1H, m); 4.28 (1H, m); 5.17 (1H, m); 7.33 (3H, m); 7.42 (1H, d); 7.75 (1H, br d); 8.76 (1H, d).

57.013:
2.18 (1H, m); 2.35 (2H, m); 2.62 (1H, m); 3.39 (1H, m); 5.07 (1H, m); 7.20 (2H, d); 7.27 (2H, d); 7.38 (1H, t); 7.75 (1H, br d); 8.75 (2H, d).

57.015:
2.11 (1H, m); 2.30 (2H, m); 2.61 (1H, m); 4.15 (1H, m); 5.02 (1H, m); 5.53 (1H, br d); 4.10 (1H, d); 7.10 (1H, m); 7.17 (2H, m); 7.27 (1H, m); 7.47 (2H, m); 7.61 (1H, d).

57.004:
4.51 (1H, dd); 5.18 (1H, dd); 5.50 (1H, ddd); 5.69 (1H, br d); 6.08 (1H, d); 6.90 (1H, d); 7.35-7.77 (7H, m).

HPLC-MS method for 57.047 and 57.070 to 57.111
Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 mm, 30×2.1 mm, Temp: 60° C., DAD Wavelength range (nm): 210 to 500, Solvent Gradient: A=water+5% MeOH+0.05% HCOOH, B=Acetonitrile+05% HCOOH: gradient: gradient: 0 min 0% B, 100% A; 1.2-1.5 min 100% B; Flow (ml/min) 0.85.

Table 58 below is a list of characterised compounds of the formula Ie. This represents formula I, wherein B is 4-chlorophenyl, A is A6, Y is $CH_2$ and R1, R3, R4, and R5 are H.

(Ie)

| Cpd no. | R2a | m.p. [° C.] | Retention time [min.] | M + H+ |
|---|---|---|---|---|
| 58.001 | —OMe | 85-93 | | |
| 58.002 | —CN | 130-136 | | |

LC-MS Method:
ACQUITY SQD Mass Spectrometer from Waters (Single quadrupole mass spectrometer)
Ionisation method: Electrospray
Polarity: positive ions
Capillary (kV) 3.00, Cone (V) 20.00, Extractor (V) 3.00, Source Temperature (° C.) 150,
Desolvation Temperature (° C.) 400, Cone Gas Flow (L/Hr) 60, Desolvation Gas Flow (L/Hr) 700
Mass range: 100 to 800 Da
DAD Wavelength range (nm): 210 to 400
Method Waters ACQUITY UPLC with the following HPLC gradient conditions
(Solvent A: Water/Methanol 9:1,0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Biological Examples

*Meloidogyne* spp. (Root-knot nematode) contact activity, preventive. Pouch test.

Filter papers (9 cm×4.5 cm) with a small pocket were placed into plastic pouches (12 cm×6 cm). One cucumber cv. Toshka seed was placed in the centre of the filter paper pocket of all the pouches needed for a test. The cucumber seeds in the pouches were treated with test solutions at 200 ppm by pipetting the solution directly over the cucumber seed in the filter paper pocket in the pouch. Prior to application, the compound solution was prepared at twice the concentration required and the egg suspension is prepared with FORL nutrient solution with 3000 eggs/0.5 ml. After applying all the treatments, 3000 eggs (in 0.5 ml of FORL nutrient solution) were pipetted into the pouches. The pouches were incubated in a moist chamber for twelve days and watered regularly to maintain good filter paper moisture essential for the growing cucumber root system. After this period, the filter paper containing the germinated cucumber seedling was removed from the plastic pouch to assess the number of galls caused by *Meloidogyne* spp. per root system.

The following compounds showed a greater than 80% reduction of galling compared to the untreated control: 57.009, 57.010, 57.011, 57.017, 57.012, 57.015, 57.014, 57.006, 57.016, 57.018, 57.020, 57.021, 57.022, 57.023, 57.024, 57.025, 57.028, 57.029, 57.030, 57.031, 57.033, 57.035, 57.036, 57.037, 57.039, 57.047, 57.048, 57.051, 57.052, 57.054, 57.055, 57.056, 57.057.

*Meloidogyne* spp. (Root-knot nematode) contact activity, preventive, drench test. Cucumber cv. Toshka seeds were sown directly into pots filled with a sandy substrate. Six days later pots were each treated with 5 ml of a WP10 suspension of the test compound at 20 ppm. Hereafter pots were inoculated with 3000 eggs of *M. incognita*. The trial was harvested fourteen days after trial application and inoculation. Root galling was assessed according to Zeck's gall index (Zeck, 1971).

The following compounds showed a greater than 80% reduction of galling compared to the untreated control: 57.001, 57.002, 57.003, 57.004, 57.005, 57.006, 57.007, 57.008, 57.010, 57.011, 57.014, 57.015, 57.016, 57.017, 57.018, 57.020, 57.021, 57.022, 57.023, 57.024, 57.025, 57.026, 57.028, 57.029, 57.031, 57.032, 57.033, 57.034, 57.035, 57.036, 57.037, 57.039, 57.040, 57.041, 57.042, 57.047, 57.048, 57.051, 57.052, 57.054, 57.055, 57.056, 57.057

*Heterodera schachtii*

0.5 ml of an aqueous solution of the test compound (200 ppm or 20 ppm) is pipetted into each of the three wells. 0.5 ml of a nematode suspension containing approximately 200-500 J2 larvae of *heterodera schachtii* are added to each well. After storing in the dark at 25° C. for 48 hours, the mobility of the larvae was assessed and averaged over the three wells. Nematodes were 0 to 40% active in wells treated with 20 ppm of compounds 57.033, 57.035, 57.036, 57.037, 57.040, 57.041, 57.043, 57.044, 57.055, 57.056, 57.057.

Nematodes were 0 to 40% active in wells treated with 200 ppm of compounds 57.007, 57.008, 57.009, 57.010, 57.011, 57.017, 57.018, 57.020, 57.022, 57.023, 57.024, 57.025, 57.028, 57.029, 57.030, 57.031, 57.039, 57.047, 57.048.

Table 59 below shows the comparison of the nematicidal activity of the cis isomers, which are the subject of this present invention with their corresponding trans isomers. The trans isomers were obtained using method P2 above and separated from their cis isomers as described in method P2d. In the table they are numbered according to their cis isomers with the suffix "trans" as shown in this example of 57-009 and 57-009trans

TABLE 59

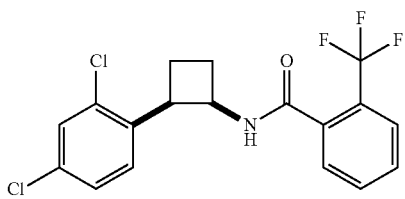

Compound 57-009
cis isomer

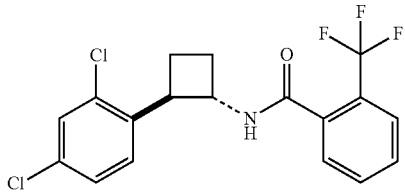

compound 57-009trans
trans isomer

TABLE 59-continued

| Cpd No. | stereo-chem-istry | Nem 1 | Nem 2 | m.p.. [° C.] | Retention time | M + H+ |
|---|---|---|---|---|---|---|
| 57.009 | cis | 100 | nt | | | |
| 57.009trans | trans | 68 | 48 | 147-148 | | |
| 57.011 | cis | 100 | 100 | | | |
| 57.011trans | trans | 84 | 64 | | 1.88 | 389 |
| 57.012 | cis | 98 | 83 | | | |
| 57.012trans | trans | 1 | nt | | 1.71 | 322 |
| 57.014 | cis | 93 | 100 | | | |
| 57.014trans | trans | 69 | 13 | 117-119 | | |

Biological Screen Nem 1. *Meloidogyne* spp. (Root-knot nematode) contact activity, preventive. Pouch test. Values are given in % galling.
Biological Screen Nem 2. *Meloidogyne* spp. (Root-knot nematode) contact activity, preventive, drench test. Values are given in % galling.
nt means not tested.

The invention claimed is:

1. Compounds of the formula I

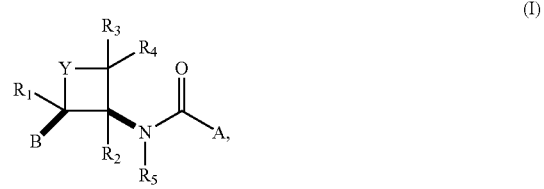

(I)

wherein

Y is O, C=O, or CR12R13;

A is a 5- or 6-membered heteroaromatic ring containing 1 to 3 heteroatoms, each independently selected from oxygen, nitrogen and sulphur, or a phenyl ring; the heteroaromatic ring or the phenyl being optionally substituted by one or more R6;

R6 is, independently of each other, halogen, cyano, C1-C4-alkyl, C1-C4-haloalkyl, C1-C4-alkoxy, C1-C4-haloalkoxy, C1-C4-haloalkylthio, C1-C4-alkoxy-C1-4-alkyl or C1-C4-haloalkoxy-C1-C4-alkyl;

R1, R2, R3, R4, R12 and R13, independently of each other, are hydrogen, halogen, cyano, C1-C4-alkyl, C1-C4-alkoxy or C1-C4-haloalkyl, R5 is hydrogen, methoxy or hydroxyl, B is phenyl substituted by one or more R8, R8 is, independently of each other, halogen, cyano or a group -L-R9, where each L is independently of each other a bond, —O—, —OC(O)—, —NR7-, —NR7CO—, —NR7S(O)n-, —S(O)n-, —S(O)nNR7-, —COO— or CONR7-, n is 0, 1 or 2, R7 is hydrogen, C1-C4-alkyl, C1-C4-haloalkyl, benzyl or phenyl, where benzyl and phenyl is unsubstituted or substituted with halogen, cyano, C1-C4-alkyl or C1-C4-haloalkyl, R9 is, independently of each other, C1-C6-alkyl, which is unsubstituted or substituted by one or more R10, C3-C6-cycloalkyl, which is unsubstituted or substituted by one or more R10, C6-C14-bicycloalkyl, which is unsubstituted or substituted by one or more R10, C2-C6-alkenyl, which is unsubstituted or substituted by one or more R10, C2-C6-alkynyl, which is unsubstituted or substituted by one or more R10, phenyl, which is unsubstituted or substituted by R10, or heteroaryl, which is unsubstituted or substituted by one or more R10, R10 is, independently of each other, halogen, cyano, C1-C4-alkyl, C1-C4-haloalkyl, C1-C4-alkoxy, C1-C4-haloalkoxy, C1-C4-alkylthio, C1-C4-haloalkylthio, C3-C6-alkenyloxy, or C3-C6-alkynyloxy, wherein B and A-CO—NR5 are cis to each other on the four-membered ring, and tautomers/isomers/enantiomers of these compounds.

2. The compound of according to claim 1 wherein Y is O or CH2;

A is a 6-membered heteroaromatic ring containing 1 to 2 nitrogen atoms, or a phenyl ring; the heteroaromatic ring or the phenyl being optionally substituted by one or more R6;

R6 is, independently of each other, halogen, cyano, C1-C4-alkyl, C1-C4-haloalkyl, or C1-C4-haloalkoxy;

R1, R2, R3, R4, and R5 are each hydrogen;

B is phenyl substituted by one or more R8;

R8 is, independently of each other, selected from halogen, cyano, C1-C4-alkyl, C1-C4-haloalkyl, C1-C4-haloalkoxy, or C3-C6-cycloalkyl.

3. The compound according to claim 1 wherein A is a 6-membered heteroaromatic ring containing 1 to 2 nitrogen atoms and having 1 to 3 substituents selected from R6, or a phenyl ring having 1 or 3 substitutents selected from R6.

4. The compound according to claim 1 wherein B is a phenyl substituted by 1 to 3 substitutents R8.

5. The compound according to claim 1 wherein B is a phenyl substituted by 1 to 3 substituents, independently selected from fluoro, chloro, trifluoromethyl, cyclopropyl, difluoromethoxy and trifluoromethoxy, A is a phenyl, pyridyl or pyrazinyl, which rings, independently of each other, are unsubstituted or substituted by 1 to 3 substituents, independently selected, from chloro, bromo, fluoro, methyl, cyano, and trifluoromethyl, Y is O or CH2, and R1, R2, R3, R4 and R5 are each hydrogen.

6. A pesticidal composition, which, in addition to comprising formulation adjuvants, comprises a pesticidal effective amount of a compound of the formula I according to claim 1.

7. The composition according to claim 6, which further comprises one or more other biologically active agents.

8. A method of controlling damage and/or yield loss caused by a pest and/or fungi which comprises applying to a pest, to a locus of a pest, or to a plant susceptible to attack by a pest and/or fungi or to a plant propagation material an effective amount of a compound of formula (I) as defined in claim 1.

9. A method for the protecting plant propagation material from damage and/or yield loss caused by a pest and/or fungi which comprises applying to the propagation material or the site, where the propagation material is planted, an effective amount of a compound of formula (I) as defined in claim 1.

10. The method according to claim 8 wherein the damage or loss is caused by a nematode pest.

11. A treated plant propagation material, wherein adhered to the plant propagation material is an effective amount of a compound of formula (I) as defined in claim 1.

12. A pharmaceutical composition for the control of helminths, arachnids or arthropodal endo- or ectoparasites which comprises a compound of formula (I) as defined in claim 1 and a physiologically tolerable carrier.

13. The composition according to claim 12 further comprising one or more other biologically active compounds.

14. A method of controlling endo- and ectoparasitic nematode infestations and infections in warm-blooded animals, which comprises injecting, topically applying or orally administering a composition according to claim 12.

15. Process for the preparation of compounds of the formula I according to claim 1, which comprises reacting a compound of the formula II

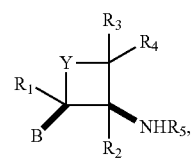

(II)

in which B, Y, $R_1$, $R_2$, $R_3$, $R_4$ and $R_5$ are as defined in claim 1, with an acylating agent of formula III

A-C(=O)—R*     (III), in which A is as defined in claim 1, and R* is halogen, hydroxyl or $C_{1-6}$ alkoxy, in the presence of a base.

16. Compounds of the formula (XIXa)

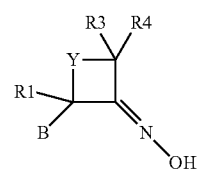

(XIXa)

wherein B, Y, R1, R3 and R4 are as defined in claim 1, where the compounds of the formulae

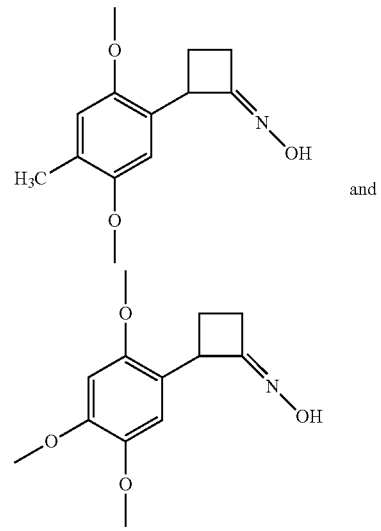

and are excluded.

17. Compounds of the formula

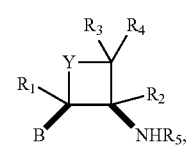

(II)

wherein B, Y, R1, R2, R3, R4 and R5 are as defined in claim 1, where the compound of the formula

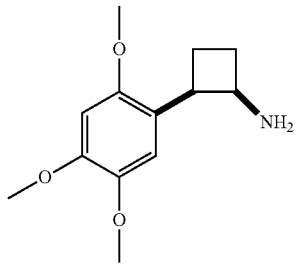

is excluded.

18. The compound according to claim 1 wherein the compound is selected from any one of compounds 1 to 118 of formula (Id)

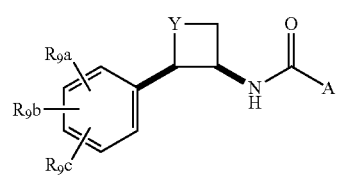

or a salt or N-oxide thereof;

wherein Y, R9a, R9b, R9c and A are as defined in the following table:

| Cpd no. | Y | R9a, R9b, R9c | A |
|---|---|---|---|
| 1 | $CH_2$ | 4—$OCF_3$ | 2,6-difluorophenyl |
| 2 | $CH_2$ | 4—$OCF_3$ | 2-methylphenyl |
| 3 | $CH_2$ | 4—$OCF_3$ | 2-($CF_3$)phenyl |
| 4 | O | 4—Cl | 2-($CF_3$)phenyl |
| 5 | $CH_2$ | 4—Cl | 2,6-difluorophenyl |
| 6 | $CH_2$ | 4—Cl | 2-($CF_3$)phenyl |
| 7 | $CH_2$ | 4—Cl | 2-($CF_3$)-pyridin-3-yl |
| 8 | $CH_2$ | 2,4—$Cl_2$ | 2,6-difluorophenyl |
| 9 | $CH_2$ | 2,4—$Cl_2$ | 2-($CF_3$)phenyl |
| 10 | O | 4—F | 2-($CF_3$)phenyl |
| 11 | $CH_2$ | 2,4—$Cl_2$ | 2-($CF_3$)-pyridin-3-yl |
| 12 | $CH_2$ | 2,4—$Cl_2$ | pyrimidin-2-yl |
| 13 | $CH_2$ | 4—Cl | pyrimidin-2-yl |
| 14 | $CH_2$ | 2—F,4—Cl | 2,6-difluorophenyl |
| 15 | $CH_2$ | 2—F,4—Cl | 2-($CF_3$)phenyl |
| 16 | $CH_2$ | 4—$OCHF_2$ | 2,6-difluorophenyl |

-continued
| Cpd no. | Y | R9a, R9b, R9c | A |
|---|---|---|---|
| 17 | CH$_2$ | 4—OCHF2 | 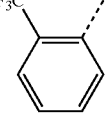 |
| 18 | CH$_2$ | 4—Cl | 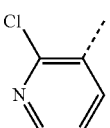 |
| 19 | CH$_2$ | 4—Cl | 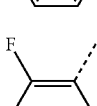 |
| 20 | CH$_2$ | 4—Cl | 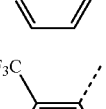 |
| 21 | CH$_2$ | 4—Cl | 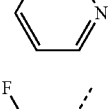 |
| 22 | CH$_2$ | 4—Cl | 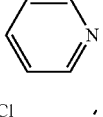 |
| 23 | CH$_2$ | 4—Cl | 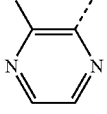 |
| 24 | CH$_2$ | 4—Cl | 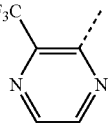 |
| 25 | CH$_2$ | 2,4—Cl2 | 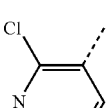 |
| 26 | CH$_2$ | 2,4—Cl2 | 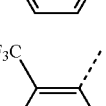 |
| 27 | CH$_2$ | 2,4—Cl2 | 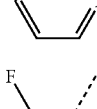 |
-continued
| Cpd no. | Y | R9a, R9b, R9c | A |
|---|---|---|---|
| 28 | CH$_2$ | 2,4—Cl2 | 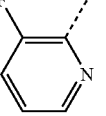 |
| 29 | CH$_2$ | 2,4—Cl2 | 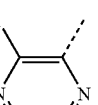 |
| 30 | CH$_2$ | 2,4—Cl2 | 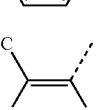 |
| 31 | CH$_2$ | 2,4—Cl2 | 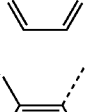 |
| 32 | CH$_2$ | 4—F | 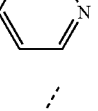 |
| 33 | CH$_2$ | 4—F | 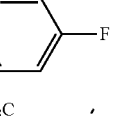 |
| 34 | CH$_2$ | 4—Br | 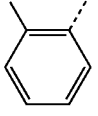 |
| 35 | CH$_2$ | 4—Br | 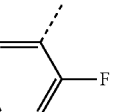 |
| 36 | not tested | 4—F | 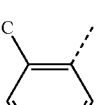 |
| 37 | CH$_2$ | 4—Br | 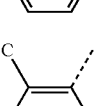 |
| 38 | CH$_2$ | 4—cPr | 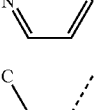 |

| Cpd no. | Y | R9a, R9b, R9c | A |
|---|---|---|---|
| 39 | CH₂ | 4—CN | 2-CF₃-pyridin-3-yl |
| 40 | CH₂ | 4—F | 3-CF₃-pyridin-2-yl |
| 41 | CH₂ | 4—F | 3-Cl-pyridin-2-yl |
| 42 | CH₂ | 4—F | 3-F-pyridin-2-yl |
| 43 | CH₂ | 4—F | 3-Cl-pyrazin-2-yl |
| 44 | CH₂ | 4—F | 3-CF₃-pyrazin-2-yl |
| 45 | CH₂ | 4—Br | 3-Cl-pyrazin-2-yl |
| 46 | CH₂ | 4—Br | 3-CF₃-pyrazin-2-yl |
| 47 | O | 2,4,6—F₃ | 2-CF₃-phenyl |
| 48 | O | 4—OCHF₂ | 2-CF₃-phenyl |
| 49 | O | 4—CF3 | 2-CF₃-phenyl |
| 50 | O | 2—F, 4—CF3 | 2-CF₃-phenyl |
| 51 | O | 2,4—F₂ | 2,6-F₂-phenyl |
| 52 | O | 2,4,6—F₃ | 2,6-F₂-phenyl |
| 53 | O | 4—F | 2,6-F₂-phenyl |
| 54 | O | 4—F | 2-CF₃-pyridin-3-yl |
| 55 | O | 2,4—F2 | 2-CF₃-phenyl |
| 56 | O | 2,4—F2 | 2-CF₃-pyridin-3-yl |
| 57 | O | 2,4,6—F3 | 2-CF₃-pyridin-3-yl |
| 58 | CH₂ | 2,4—F2 | 2-CF₃-phenyl |
| 59 | CH₂ | 2,4—F2 | 3-CF₃-pyridin-2-yl |
| 60 | CH₂ | 2,4—F2 | 2-CF₃-pyridin-3-yl |

-continued
| Cpd no. | Y | R9a,R9b, R9c | A |
|---|---|---|---|
| 61 | CH₂ | 2,4—F2 | 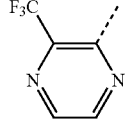 |
| 62 | CH₂ | 2—Cl, 4—CF3 | 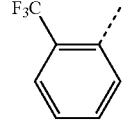 |
| 63 | CH₂ | 2—Cl, 4—CF3 |  |
| 64 | CH₂ | 2—Cl, 4—CF3 |  |
| 65 | CH₂ | 2—Cl, 4—CF3 |  |
| 66 | CH₂ | 2—F, 4—CF3 |  |
| 67 | CH₂ | 2—F, 4—CF3 |  |
| 68 | CH₂ | 2—F, 4—CF3 | 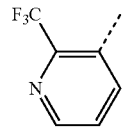 |
| 69 | CH₂ | 2—F, 4—CF3 | 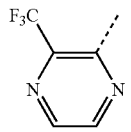 |
| 70 | CH₂ | 2,4—Cl2 | 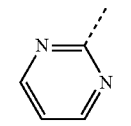 |
| 71 | CH₂ | 2,4—Cl2 | 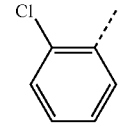 |
-continued
| Cpd no. | Y | R9a,R9b, R9c | A |
|---|---|---|---|
| 72 | CH₂ | 2,4—Cl2 | 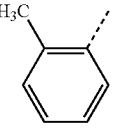 |
| 73 | CH₂ | 2,4—Cl2 | 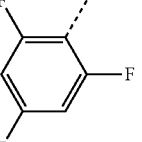 |
| 74 | CH₂ | 2,4—Cl2 | 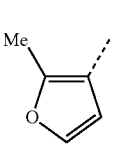 |
| 75 | CH₂ | 2,4—Cl2 | 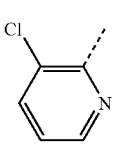 |
| 76 | CH₂ | 2,4—Cl2 | 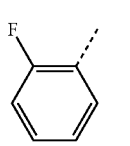 |
| 77 | CH₂ | 2,4—Cl2 | 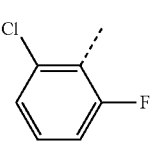 |
| 78 | CH₂ | 2,4—Cl2 | 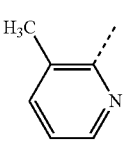 |
| 79 | CH₂ | 2,4—Cl2 | 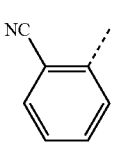 |
| 80 | CH₂ | 2,4—Cl2 | 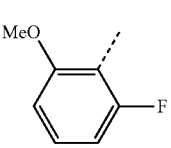 |
| 81 | CH₂ | 2,4—Cl2 | 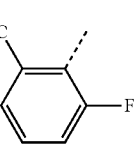 |
| 82 | CH₂ | 2,4—Cl2 | 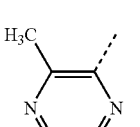 |

-continued
| Cpd no. | Y | R9a,R9b, R9c | A |
|---|---|---|---|
| 83 | CH₂ | 2,4—Cl2 | 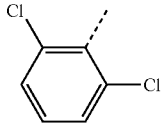 |
| 84 | CH₂ | 2,4—Cl2 | 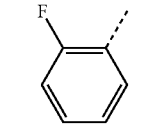 |
| 85 | CH₂ | 2,4—Cl2 | 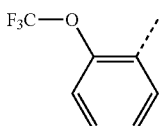 |
| 86 | CH₂ | 2,4—Cl2 | 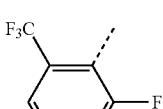 |
| 87 | CH₂ | 2,4—Cl2 | 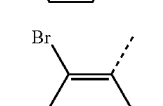 |
| 88 | CH₂ | 2,4—Cl2 | 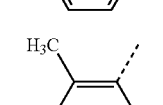 |
| 89 | CH₂ | 2,4—Cl2 | 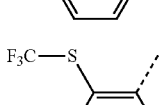 |
| 90 | CH₂ | 2,4—Cl2 | 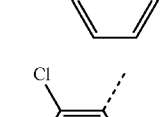 |
| 91 | CH₂ | 4—Cl | 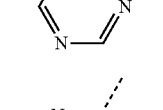 |
| 92 | CH₂ | 4—Cl | 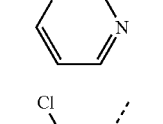 |
| 93 | CH₂ | 4—Cl | 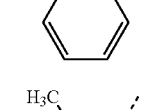 |
-continued
| Cpd no. | Y | R9a,R9b, R9c | A |
|---|---|---|---|
| 94 | CH₂ | 4—Cl | 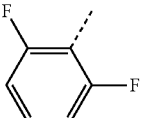 |
| 95 | CH₂ | 4—Cl | 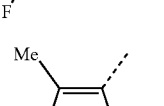 |
| 96 | CH₂ | 4—Cl | 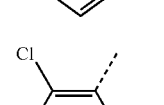 |
| 97 | CH₂ | 4—Cl | 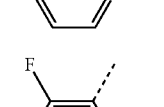 |
| 98 | CH₂ | 4—Cl | 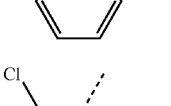 |
| 99 | CH₂ | 4—Cl | 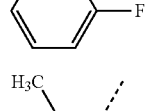 |
| 100 | CH₂ | 4—Cl | 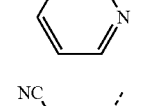 |
| 101 | CH₂ | 4—Cl | 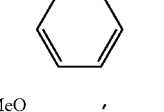 |
| 102 | CH₂ | 4—Cl | 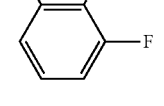 |
| 103 | CH₂ | 4—Cl | 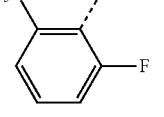 |
| 104 | CH₂ | 4—Cl | 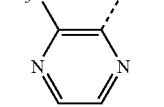 |

-continued

| Cpd no. | Y | R9a,R9b, R9c | A |
|---|---|---|---|
| 105 | CH₂ | 4—Cl | 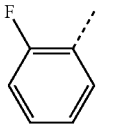 |
| 106 | CH₂ | 4—Cl | 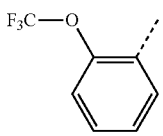 |
| 107 | CH₂ | 4—Cl | 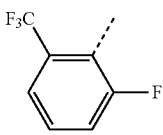 |
| 108 | CH₂ | 4—Cl | 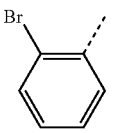 |
| 109 | CH₂ | 4—Cl | 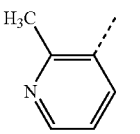 |
| 110 | CH₂ | 4—Cl | 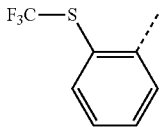 |
| 111 | CH₂ | 4—Cl | 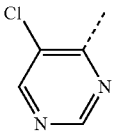 |
| 112 | CH₂ | 2—Cl, 4—F | 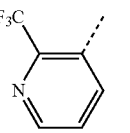 |
| 113 | CH₂ | 2—Cl, 4—F | 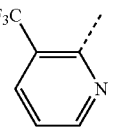 |
| 114 | CH₂ | 2—Cl, 4—Br | 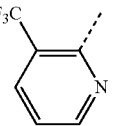 |
| 115 | CH₂ | 2,4—F2 | 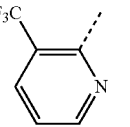 |
| 116 | CH₂ | 4—OCF3 | 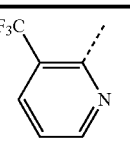 |
| 117 | CH₂ | 2—F, 4—Cl | 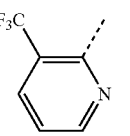 |
| 118 | CH₂ | 2—Cl, 4—F | 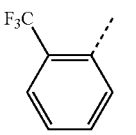 | and wherein any one of R9a, R9b and R9c is hydrogen unless otherwise defined.

19. The compound, or a salt or N-oxide thereof, according to claim 1 selected from the group consisting of:

N-[(1,2 cis)-2-(4-chlorophenyl)cyclobutyl]-2-(trifluoromethyl)pyridine-3-carboxamide;
N-[(1,2 cis)-2-(2,4-dichlorophenyl)cyclobutyl]-2,6-difluorobenzamide;
N-[(1,2 cis)-2-(2,4-dichlorophenyl)cyclobutyl]-2-(trifluoromethyl)benzamide;
N-[(1,2 cis)-2-(2,4-dichlorophenyl)cyclobutyl]-2-(trifluoromethyl)pyridine-3-carboxamide;
N-[(1,2 cis)-2-(2,4-difluorophenyl)cyclobutyl]-2-(trifluoromethyl)benzamide;
N-[(1,2 cis)-2-(2,4-difluorophenyl)cyclobutyl]-2-(trifluoromethyl)pyridine-3-carboxamide;
N-[(1,2 cis)-2-(2,4-difluorophenyl)cyclobutyl]-3-(trifluoromethyl)pyrazine-2-carboxamide;
N-[(1,2 cis)-2-[2-chloro-4-(trifluoromethyl)phenyl]cyclobutyl]-3-(trifluoromethyl)pyridine-2-carboxamide;
N-[(1,2 cis)-2-[2-chloro-4-(trifluoromethyl)phenyl]cyclobutyl]-2-(trifluoromethyl)pyridine-3-carboxamide;
N-[(1,2 cis)-2-[2-chloro-4-(trifluoromethyl)phenyl]cyclobutyl]-3-(trifluoromethyl)pyrazine-2-carboxamide;
N-[(1,2 cis)-2-[2-fluoro-4-(trifluoromethyl)phenyl]cyclobutyl]-2-(trifluoromethyl)benzamide;
N-[(1,2 cis)-2-[2-fluoro-4-(trifluoromethyl)phenyl]cyclobutyl]-3-(trifluoromethyl)pyridine-2-carboxamide;
N-[(1,2 cis)-2-[2-fluoro-4-(trifluoromethyl)phenyl]cyclobutyl]-2-(trifluoromethyl)pyridine-3-carboxamide;
N-[(1,2 cis)-2-[2-fluoro-4-(trifluoromethyl)phenyl]cyclobutyl]-3-(trifluoromethyl)pyrazine-2-carboxamide;
2-(trifluoromethyl)-N-[(2,3 cis)-2-(2,4,6-trifluorophenyl)oxetan-3-yl]benzamide;
2,6-difluoro-N-[(2,3 cis)-2-(2,4,6-trifluorophenyl)oxetan-3-yl]benzamide;
N-[(2,3 cis)-2-(2,4-difluorophenyl)oxetan-3-yl]-2-(trifluoromethyl)benzamide;
N-[(2,3 cis)-2-(2,4-difluorophenyl)oxetan-3-yl]-2-(trifluoromethyl)pyridine-3-carboxamide;
3-chloro-N-[(1,2 cis)-2-(2,4-dichlorophenyl)cyclobutyl]pyrazine-2-carboxamide;
N-[(1,2 cis)-2-(2,4-dichlorophenyl)cyclobutyl]-3-(trifluoromethyl)pyridine-2-carboxamide;

3-chloro-N-[(1,2 cis)-2-(2,4-dichlorophenyl)cyclobutyl] pyridine-2-carboxamide;

N-[(1,2 cis)-2-(2,4-dichlorophenyl)cyclobutyl]-2-methylpyridine-3-carboxamide;

N-[(1,2 cis)-2-(2,4-dichlorophenyl)cyclobutyl]-3-methylpyridine-2-carboxamide;

N-[(1,2 cis)-2-(2,4-difluorophenyl)cyclobutyl]-2-(trifluoromethyl)pyridine-3-carboxamide;

2-Chloro-N-[(1,2 cis)-2-(2,4-dichloro-phenyl)-cyclobutyl]-nicotinamide;

N-[(1,2 cis)-2-(2-chloro-4-fluoro-phenyl)cyclobutyl]-2-(trifluoromethyl)pyridine-3-carboxamide;

N-[(1,2 cis)-2-(2-chloro-4-fluoro-phenyl)cyclobutyl]-3-(trifluoromethyl)pyridine-2-carboxamide;

N-[(1,2 cis)-2-(4-bromo-2-chloro-phenyl)cyclobutyl]-3-(trifluoromethyl)pyridine-2-carboxamide;

N-[(1,2 cis)-2-(2,4-difluorophenyl)cyclobutyl]-3-(trifluoromethyl)pyridine-2-carboxamide;

N-[(2,3 cis)-2-(2,4-difluorophenyl)oxetan-3-yl]-2-(trifluoromethyl)benzamide;

N-[(1,2 cis)-2-(4-methoxyphenyl)cyclobutyl]-3-(trifluoromethyl)pyridine-2-carboxamide;

N-[(1,2 cis)-2-(4-chloro-2-fluoro-phenyl)cyclobutyl]-3-(trifluoromethyl)pyridine-2-carboxamide; and N-[(1,2 cis)-2-(2-chloro-4-fluoro-phenyl)cyclobutyl]-2-(trifluoromethyl)benzamide.

\* \* \* \* \*